US006171244B1

(12) United States Patent
Finger et al.

(10) Patent No.: US 6,171,244 B1
(45) Date of Patent: Jan. 9, 2001

(54) ULTRASONIC SYSTEM AND METHOD FOR STORING DATA

(75) Inventors: David J. Finger, San Jose; Ismayil M. Guracar, Redwood City; D. Grant Fash, III, Saratoga; Shahrokh Shakouri, San Jose, all of CA (US)

(73) Assignee: Acuson Corporation, Mountain View, CA (US)

( * ) Notice: Under 35 U.S.C. 154(b), the term of this patent shall be extended for 0 days.

(21) Appl. No.: 09/001,489

(22) Filed: Dec. 31, 1997

(51) Int. Cl.$^7$ ........................................................ A61B 8/00

(52) U.S. Cl. ............................................................. 600/437

(58) Field of Search .................................. 600/443, 444, 600/445, 446, 447, 449, 438, 454

(56) References Cited

U.S. PATENT DOCUMENTS

| | | |
|---|---|---|
| 4,271,842 | 6/1981 | Specht et al. . |
| 4,662,222 | 5/1987 | Johnson . |
| 4,694,680 | 9/1987 | Takeuchi et al. . |
| 5,156,152 | 10/1992 | Yamazaki et al. . |
| 5,322,066 | 6/1994 | Miyataka et al. . |
| 5,396,890 | 3/1995 | Weng . |
| 5,409,007 * | 4/1995 | Saunders et al. ...................... 600/443 |
| 5,474,073 | 12/1995 | Schwartz et al. . |
| 5,477,858 | 12/1995 | Norris et al. . |
| 5,483,963 | 1/1996 | Butler et al. . |
| 5,485,842 | 1/1996 | Quistgaard . |
| 5,492,125 | 2/1996 | Kim et al. . |
| 5,524,629 * | 6/1996 | Mahony ................................ 600/447 |
| 5,588,032 | 12/1996 | Johnson et al. . |
| 5,645,066 | 7/1997 | Gandini et al. . |
| 5,709,206 | 1/1998 | Teboul . |
| 5,709,209 | 1/1998 | Friemel et al. . |
| 5,715,823 | 2/1998 | Wood et al. . |

(List continued on next page.)

FOREIGN PATENT DOCUMENTS 0 829 735 A2  3/1998  (EP) .

OTHER PUBLICATIONS

Basoglu et al; "A Programmable Ultrasound Subsystem for Native Image Processing"; SPIE vol. 2707; pp. 378–388 (1996).
Apollo VP3; VIA WWW page print out; Nov. 10, 1997.
Accelerated Graphics Port; AGP; tutorial and AGP benefits; WWW page print out; Nov. 14, 1997.
Intel 440LX; AGP set and product brief; Intel WWW page print out; Nov. 4, 1997.

*Primary Examiner*—Marvin M. Lateef
*Assistant Examiner*—Maulin Patel
(74) *Attorney, Agent, or Firm*—Craig A. Summerfield, Esq.; Brinks Hofer Gilson & Lione

(57) ABSTRACT

An apparatus and method for processing ultrasound data is provided. The apparatus includes an interface operatively connected to a memory, a programmable single instruction multiple data processor (or two symmetric processors), a source of acoustic data (such as a data bus) and a system bus. The memory stores data from the processor, ultrasound data from the source, and data from the system bus. The processor has direct access to the memory. Alternatively, the system bus has direct access to the memory. The interface device translates logically addressed ultrasound data to physically addressed ultrasound data for storage in a memory. The translation is the same for data from both the processor and the source for at least a portion of a range of addresses. The memory stores both ultrasound data and various of: beamformer control data, instruction data for the processor, display text plane information, control plane data, and a table of memory addresses. One peripheral connects to the ultrasound apparatus. An interface adapter, powered from the ultrasound apparatus, translates information transferred between the peripheral and the ultrasound apparatus. The adapter connects non-standard peripherals to various standard interfaces on the ultrasound apparatus.

41 Claims, 8 Drawing Sheets

U.S. PATENT DOCUMENTS

| | | | |
|---|---|---|---|
| 5,779,641 | * 7/1998 | Hatfiled et al. | 600/443 |
| 5,787,889 | 8/1998 | Edwards et al. . | |
| 5,795,296 | 8/1998 | Pathak et al. . | |
| 5,795,297 | 8/1998 | Daigle . | |
| 5,810,747 | 9/1998 | Brudny et al. . | |

* cited by examiner

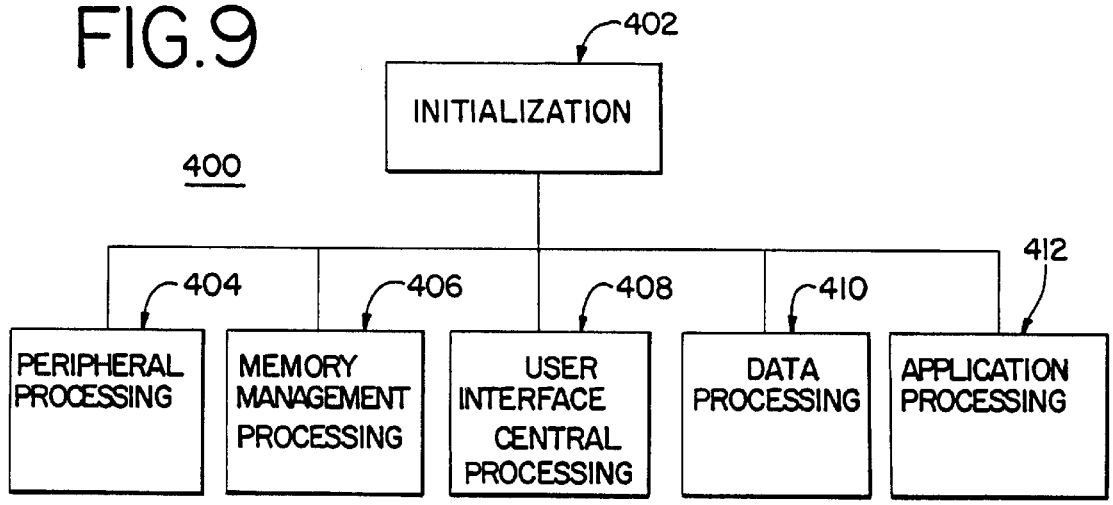
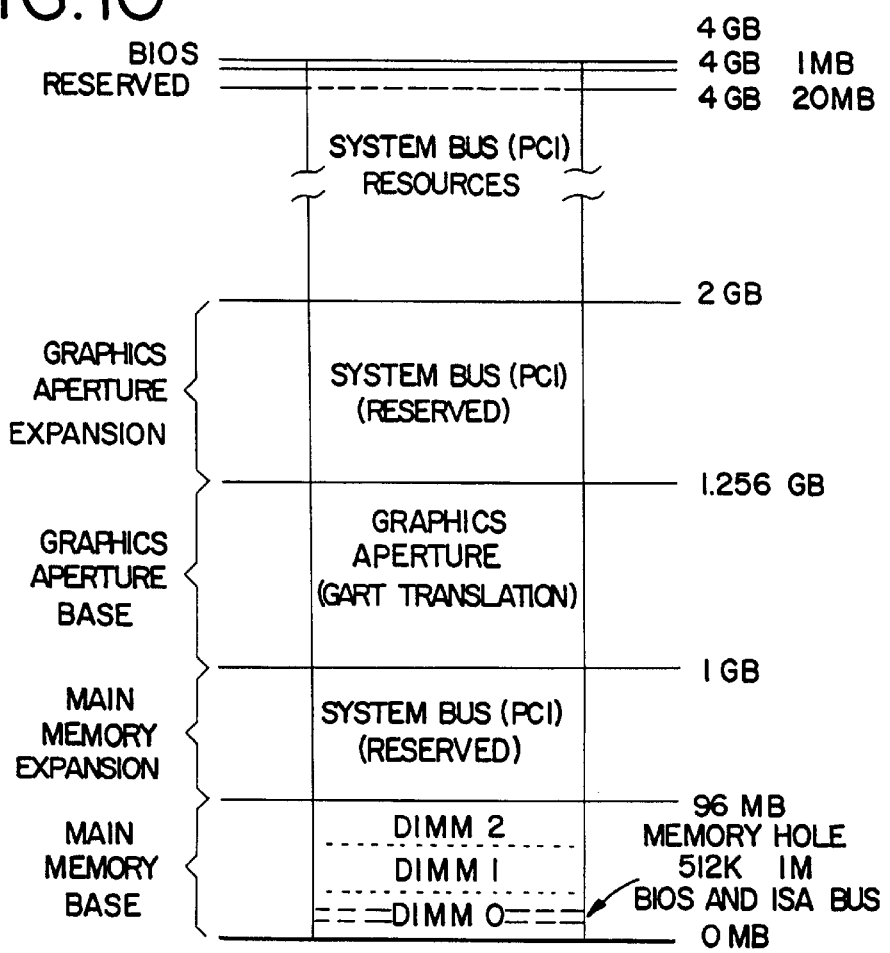

ULTRASONIC SYSTEM AND METHOD FOR STORING DATA

BACKGROUND

This invention relates to an ultrasound system and method for processing data. In particular, the method and system provide for processing, transferring, and storing ultrasound data, control data, and other information.

Ultrasound systems acquire, process, and store acoustic information. The acoustic information is used to generate various types of images and other data. Typically, ultrasound imaging systems include several dedicated data processing structures, including one or more digital signal processors (DSP) for processing the acoustic data and one or more microprocessors for system control. The control microprocessors provide control instructions to the data processing structures. The control instructions are generated in response to operating system software, user interface input, and other communication and control software. One or more separate memory blocks provide bulk storage for CINE operations, storing acoustic data generated by the various data processing structures. The memory blocks are designed to support the specific volume and bandwidth of the real time data stored in and retrieved from them. A separate memory is used for storing the microprocessor software. As a result, the microprocessors do not have direct and efficient access to acoustic data during real time operation of the ultrasound system, and many different memories are required.

Another example of the separation of memories is the use of various display refresh memory planes for generating an image. Ultrasound systems typically employ separate display refresh memory planes for each of combination control information, text and graphics information, waveform information, and image information. The stored information is output from each of these memories at a constant rate to update and refresh the display. Due to different reconstruction and display requirements for the different types of data, the refresh memory planes are separated. Text and graphics information is generally constructed by a microprocessor and written into the text and graphics refresh memory plane. Image and waveform data are generally constructed by some combination of dedicated hardware and DSP processing. The image and waveform data are then stored in their respective memory planes. The output from the refresh memory planes is combined and displayed.

One example of an ultrasound system is disclosed in U.S. Pat. No. 4,662,222 (the '222 patent). The '222 patent describes various models for reconstructing an acoustic image using inverse scattering techniques. Beginning at column 19, line 14, the system for generating the acoustic image is described. The system includes a CPU and an array processor to control the electronic system in accordance with the flowcharts shown in FIGS. 6A–6F. At lines 25–28, the disclosure notes that "special purpose computational hardware should be constructed to incorporate the flow diagrams of FIGS. 6A–6F." The appendix of the '222 patent discloses a program to solve the inverse scattering models by the array processor. The CPU's control of the system to solve the inverse scattering models is then described with reference to FIGS. 6A–6F.

Some ultrasound systems combine various memory structures and processing structures. For example, U.S. Pat. No. 5,492,125 discloses two multi-processors for processing acoustic data. The multi-processors share a memory. The memory is accessed through a cross-bar. One multi-processor receives acoustic data and partially processes the data. The partially processed data is stored in the shared memory. The other multi-processor obtains the partially processed data and completes the processing.

Multi-processors are used in systems other than ultrasound systems. For example, multi-processors are used in personal computing. Various multi-processors are known, such as Pentium Pro®, Pentium II®, and other 686 class microprocessors that support multi-processing, and that use single instruction multiple data processing. For use with graphics intensive computers, interface devices such as the Intel® Accelerated Graphics Port chip set are used to provide high speed interactions between graphic accelerators, multi-processors and memories.

SUMMARY

The present invention is defined by the following claims, and nothing in this section should be taken as a limitation on those claims. By way of introduction, the preferred embodiment described below includes an apparatus and method for processing ultrasound data. The apparatus includes an interface operatively connected to a memory, a processor, a source of acoustic data (such as a data bus) and a system bus. The memory stores data from the processor, ultrasound data from the source, and data from the system bus. The processor has direct access to the memory. In another embodiment, the system bus has direct access to the memory.

In other embodiments, a memory stores both ultrasound date and various of: beamformer control data, instruction data for the processor, display text plane information, control plane data, and a table of memory addresses.

Other embodiments are possible. Further aspects and advantages of the invention are discussed below in conjunction with the preferred embodiments.

BRIEF DESCRIPTION OF THE DRAWINGS

FIG. 9 is a flow chart representation of a processor functions.

FIG. 10 is a representation of a memory map of one embodiment.

DETAILED DESCRIPTION OF PREFERRED EMBODIMENTS

Figure 1:
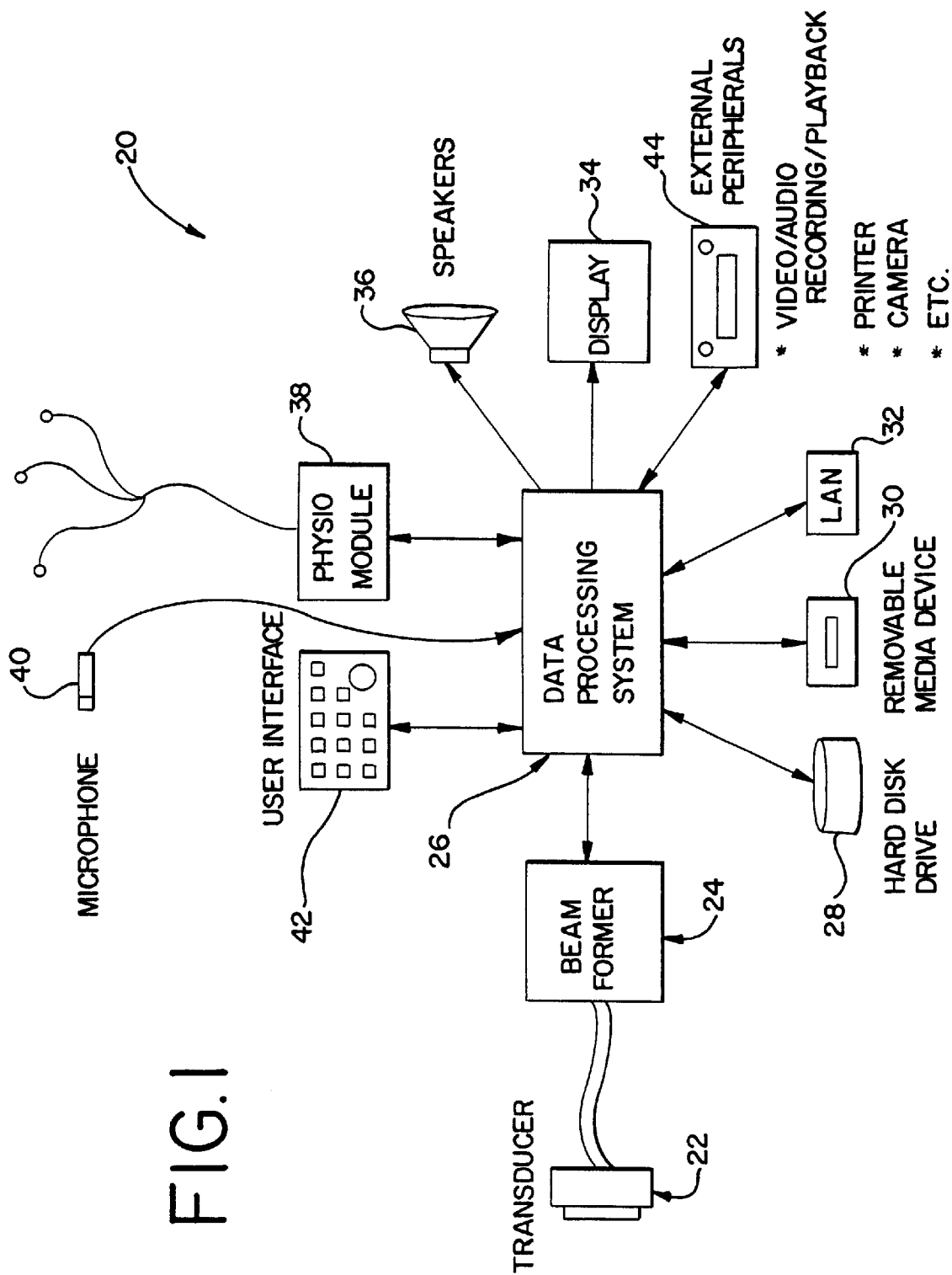
FIG. 1 is a block diagram of an ultrasound imaging system, including various peripheral components.

Referring to FIG. 1, a preferred embodiment of an ultrasound system according to the present invention is generally shown at 20. The flexible system 20 is described below, first with reference to the structure of the system 20, and then with a reference to several examples of the operation of the system 20. Other structures and uses of the system 20 are intended to be covered by the claims, which define the invention.

I. Structure:

A. General:

The system 20 includes a transducer 22, a beamformer 24 and a data processing system 26. The system 20 also includes various peripherals, such as a hard disk drive 28, a removable media device 30 (e.g. a magneto optical disk drive), a local area network 32, a display 34, a speaker 36, a physio module 38, a microphone 40, a user interface 42 and other external peripherals 44. The other external peripherals include video or audio recording and playback devices, printers, cameras, and other devices. The peripherals may include analog or digital video or audio inputs and outputs. The physio module 38 preferably includes an EGG, phono, pulse, respiration and one or more auxiliary DC-coupled input channels (e.g. DC-A, DC-B, DC-C and DC-D). Preferably, the data processing system 26 controls operation of the peripherals. The system 20 may include no peripherals or any subset of these peripherals.

The data processing system 26 includes a centralized memory for storing microprocessor code and data (software or algorithms) and concurrently storing various subsystem data. The subsystem data includes acoustic image data, video data, audio data, physio data, waveform data, text and graphics data, and other subsystem data.

As used herein, the term ultrasound or acoustic image data encompasses data derived from the transmission of acoustic energy and used to generate an image or audio output in one or more of various modes, such as B-mode, M-mode, color Doppler mode (velocity, variance or energy), spectral Doppler mode (spectrum, derived waveform or audio) and other modes. Ultrasound image data includes acoustic data from the beamformer 24 (e.g. in phase and quadrature data or real value data), fundamental or harmonic frequency based data, or acoustic data at various stages of processing (e.g. detected data, filtered data, weighted data, thresholded data, video data (compressed or uncompressed), combined data, and other processed data derived from acoustic data from the beamformer). The type of ultrasound image data (the stage of processing of the data) is referred to herein by the type of processing, the source or the component used to process the data. For example, harmonic data is ultrasound image data associated with harmonic frequencies of transmitted fundamental frequencies. As another example, beamformer data is ultrasound image data provided by a beamformer. Ultrasound data includes ultrasound image data, audio data (e.g. physio audio, microphone audio and VCR audio), waveform, physio, video (compressed or uncompressed), text and graphics, patient and control data used or generated in an ultrasound system.

The data processing system 26 also includes a microprocessor or parallel microprocessors in a symmetric multiprocessing structure for controlling the system and processing ultrasound image data stored in the centralized memory. The microprocessor operates in response to or executes instruction code and data also stored in the memory.

Based on control instructions from the data processing system 26, the beamformer 24 generates electrical signals. The electrical signals are applied to the transducer 22. The transducer 22 transmits acoustic energy and receives echo signals. Electrical signals corresponding to the echo signals are provided to the beamformer 24 from the transducer 22. The beamformer outputs ultrasound image data, such as in phase and quadrature (I and Q) data associated with a plurality of ranges along one or more scan lines.

The data processing system 26 processes and stores the ultrasound image data from the beamformer 24. Processing includes altering the data before, after or as part of a reconstruction or scan conversion and output to the display 34. For example, color Doppler information is detected from the I and Q ultrasound image data, and the detected ultrasound image data is stored. The stored ultrasound image data is then temporally or spatially filtered or otherwise processed. The processed ultrasound image data is also stored and output for reconstruction.

Other than the beamformer 24, one or more peripherals may provide ultrasound data to the data processing system 26. The external peripherals may also receive ultrasound data from the data processing system 26, such as audio data or video ultrasound image data. The hard disk drive 28 and the removable media device 30 provide and store software, ultrasound data and other information for the data processing system 26. A local area network (LAN) also supports the transfer of software or ultrasound data to or from the data processing system 26. For example, operating system code, patient data, parameter data, control data or image data is transferred. The user interface 42 provides or receives information about the status of the various user controls or displays (lights or other secondary displays on the user interface 42). The physio module 38 provides patient physiological data and event (trigger) information to the data processing system 26, as well as the state of any user controls located on the physio module 38. Various physio modules 38 may be used, such as an ECG or respiration device. Data for operation of the physio module 38 is communicated from the data processing system 26 or another source. The microphone 40 allows for voice activated control of one or more user selectable functions as well as the input of patient data, such as verbal annotations. Information, such as ultrasound data, control and parameter information, or patient information may be provided from any of these or other peripherals.

Figure 2:
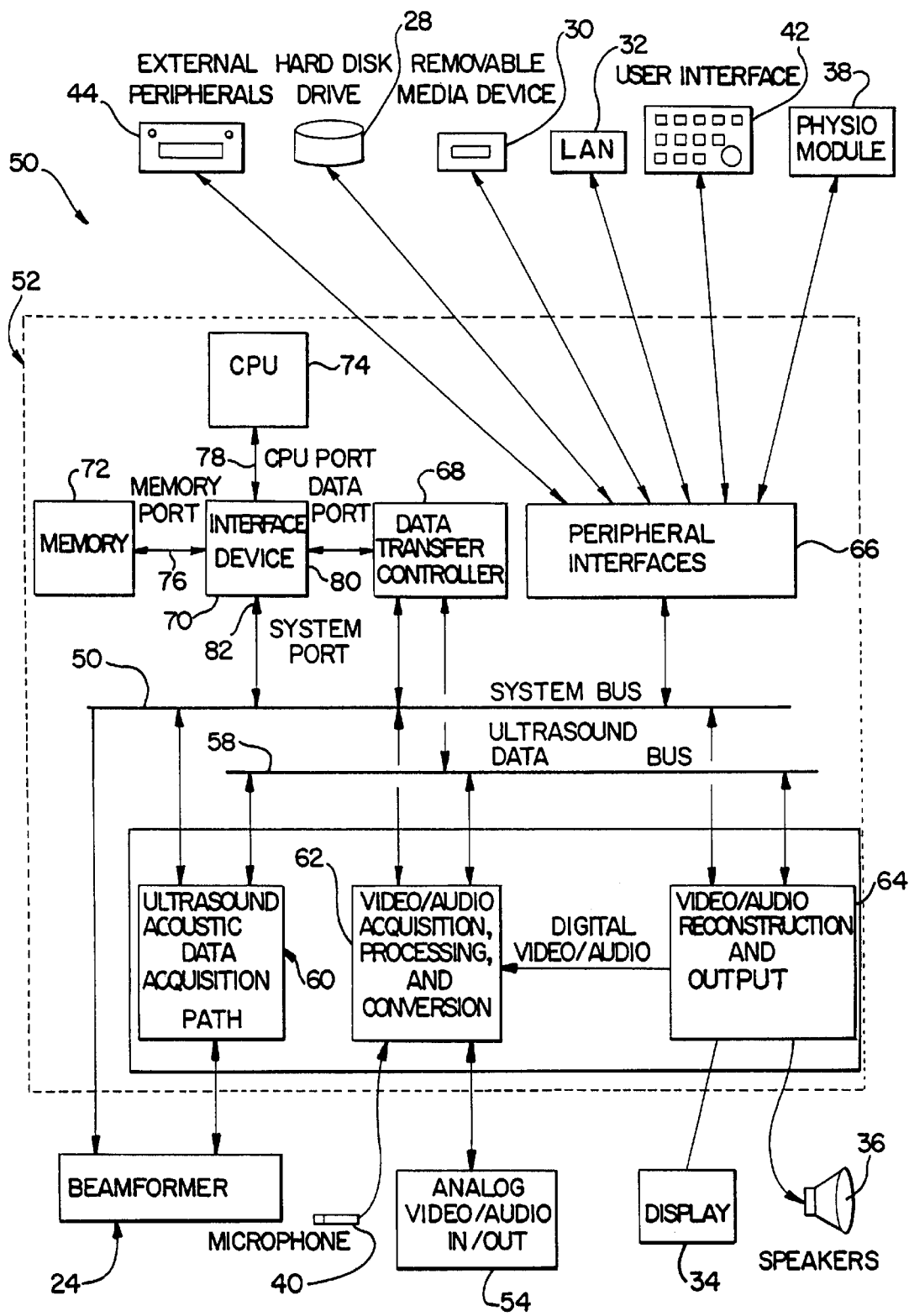
FIG. 2 is a block diagram of a data processing system of FIG. 1, including various peripheral components.

B. Data Processing System:

Referring to FIG. 2, a preferred embodiment of an ultrasound system according to the present invention is shown generally at 50. As used herein, an ultrasound system or apparatus 50 includes no, one or more peripherals. Likewise, the ultrasound apparatus or system 50 may include or exclude the beamformer 24. The system 50 preferably includes a data processing system 52, the beamformer 24, and various peripherals. The various peripherals include one or more of the hard disk drive 28, the removable media device 30, the LAN 32, the display 34, the speakers 36, the physio module 38, the microphone 40, the user interface 42, the external peripherals 44, an analog video or audio peripheral 54 and any other peripherals. Preferably, the beamformer 24 includes a multiplexer for switching between receive and transmit processing. The beamformer 24 comprises transmit and receive beamformers. In this embodiment, the receive beamformer is operatively connected to provide acoustic data, and both transmit and receive beamformers receive and are responsive to control and parameter information from the data processing system 52.

The data processing system 52 includes various ultrasound data paths and system data paths. As used herein, a data path is one or more components for receiving, processing or transferring data. Any of these various data paths may be responsive to information from other data paths.

As used herein, the term "responsive to" is intended to broadly cover any situation where a first component alters its operation in response to a signal generated by a second component whether directly or indirectly. Thus, the first component is said to be responsive to the second when the first component responds directly to an output signal of the second component. Similarly, the first component is responsive to the second if intermediate components or processors alter or modify a signal of the second component before it is applied as an input to the first component.

The data processing system 52 includes a system bus 56 and an ultrasound data bus 58. An ultrasound acoustic data acquisition path 60, a video/audio acquisition, processing and conversion path 62 (video/audio acquisition data path 62), and a video/audio reconstruction and output path 64 are connected to both the system data bus 56 and the ultrasound data bus 58. These connections allow the transfer of ultrasound data or system communication, control and parameter data between various components of the system 50. The ultrasound data acquisition path 60 also connects with the beamformer 24. The video/audio acquisition path 62 preferably also connects with the analog video/audio peripheral 54, the microphone 40 and the video/audio reconstruction path 64. The video/audio reconstruction path 64 also connects with the display 34 and the speakers 36. The system bus 56 also connects with the beamformer 24 and one or more peripheral interfaces 66.

A data transfer control device 68 also connects to both the system bus 56 and the ultrasound data bus 58. An interface device 70 connects to the data transfer controller 68, the system bus 56, a memory 72, and a CPU 74.

Figure 13:
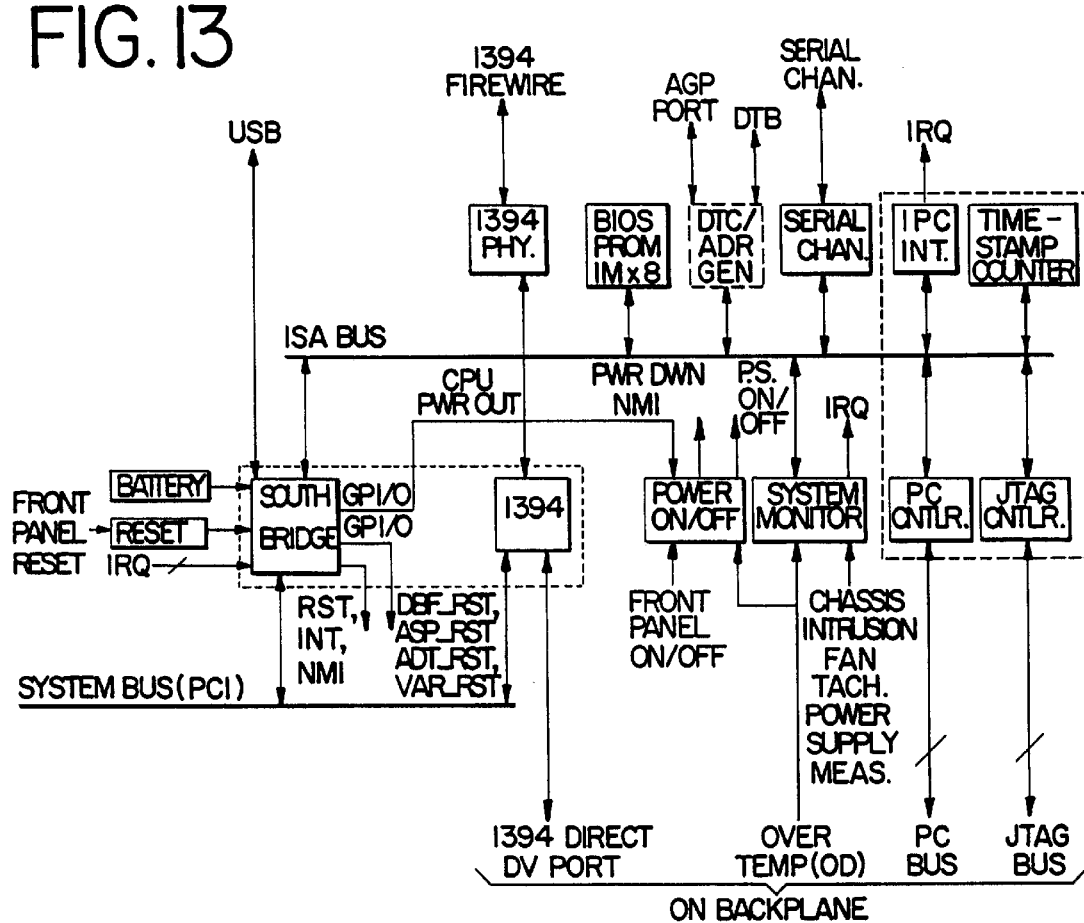
FIG. 13 is a block diagram of one preferred embodiment of a south bridge configuration.
Figure 14:
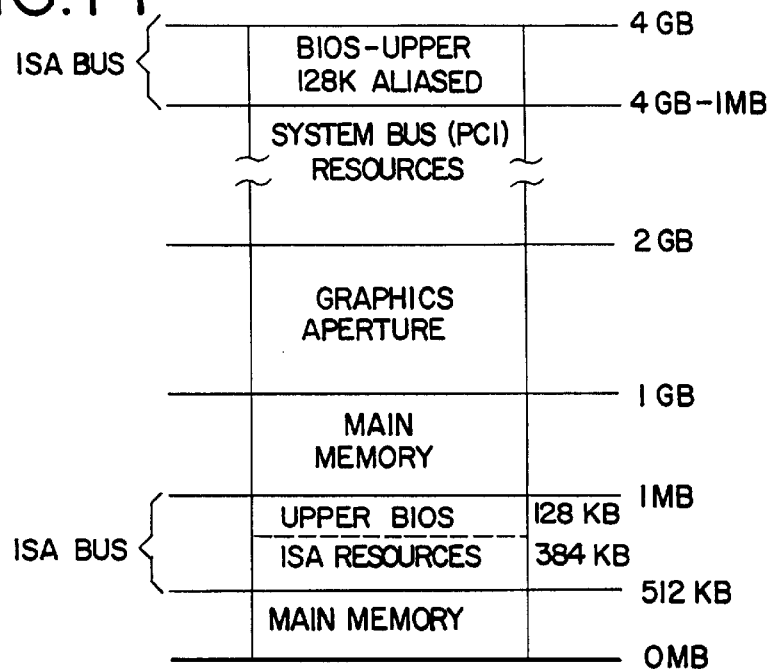
FIG. 14 is a representation of a memory map of one embodiment.

In one preferred embodiment, the various components of the data processing system 52 are on three boards (a mother board and two daughter boards). For example, the data transfer control device 68, the interface device 70, the memory 72, the CPU 74 and the peripheral interfaces 66 are located on the mother board, so that these components (e.g. the interface device 70 and the south bridge (see appendix C and FIG. 13) of the peripheral interfaces 66) are grouped together. In this example, the ultrasound acoustic data acquisition path 60 and the video/audio acquisition data path 62 are on one daughter board, and the video/audio reconstruction path 64 is on the other daughter board. Other component portioning may be used.

The interface device 70 controls access to the memory 72. Preferably, the interface device 70 is a quad port or other bridge device, such as the Intel® 82443LX, Intel® 440BX, or a Via Technologies Inc. VT82C597 PCI Accelerated Graphics Port (AGP) controllers. AGP is a specification or protocol prepared by Intel®. The interface device 70 preferably includes a physical address generator for controlling the memory 72. Other devices with more or fewer ports operating pursuant to the AGP or other specifications may be used (e.g. three ports or a PCI local bus protocol).

The interface device 70 interfaces between the memory 72, the CPU 74, the data transfer controller 68 and the system bus 56 through a memory port 76, a CPU port 78, a data port 80 and a system port 82, respectively. As used herein, a port is a connection or other interface for the transfer of data to or from a component. Preferably, the CPU port 78 comprises a microprocessor host interface with at least a 60 Mbytes/sec connection (e.g. 64 bit data path at 96 MHz). Preferably, the memory port 76 comprises a 64 bit wide data path with a 64 or 96 MHz clock with at least a 190 Mbytes/sec connection. The system port 82 comprises a PCI bus interface with at least a 30 Mbytes/sec connection (e.g. 32 bit data path at 32 MHz). The data port 80 comprises an AGP interface with at least a 100 Mbytes/sec connection (e.g. 32 bit data path at 64 MHz). The data port complies with Intel's Accelerated Graphics Port Interface Specification (revision 1.0 or later), but in alternative embodiments may employ any data transfer mechanism meeting the bandwidth and requirements discussed above or other appropriate requirements. Preferably, the data port 80 supports burst transfers of packets of ultrasound data with logical and implicit sequential addressing of successive data values to facilitate high through put and transfer efficiency.

The bandwidths discussed above are approximations and may vary as a function of various factors, including programming and system capabilities. Other effective bandwidths, bus widths, and clock rates may be used. Preferably, synchronization signals are used for transferring data between two different clock domains (e.g. 64 MHz to or from 48 MHz).

Alternatively, the interface 70 comprises other port designs, such as supporting different protocols, different connection speeds or different data widths. For example, a three port device without a data port 80 is used. In this example, the ultrasound data bus is eliminated and ultrasound data transfers are performed over the system bus 56.

The interface device 70 arbitrates between ports, translates interface signals, buffers data, controls the memory 72, routes data between the various ports and any sub-set of these functions. Preferably, the interface device 70 is operable to transfer data between the CPU port 78 and the memory or system ports 76 and 82, and to transfer data between the system or data ports 82 and 80 and the memory port 76. In alternative embodiments, the interface device 70 transfers between the CPU and data ports 78 and 80 or between the data and system ports 80 and 82.

The interface device 70 provides direct access to the memory 72 from the CPU port 78, the data port 80, and the system port 82. The CPU 74 can directly fetch instructions from memory 12 for execution, and data for processing. The memory 72 is accessed by the CPU 74 as standard random access memory in the CPU's 74 memory address space. Preferably, the access is formatted for pipelined addressing of four or more quad words or other sequences of data for improved throughput.

Accesses to the memory 72 from the system port 82 also support direct memory read and write access through single read or write transactions on the system bus 56 in the memory's 72 address space. Preferably, the system port 82 of the interface device 70 supports and controls (e.g. arbitration time out, parking and configuration cycle generation) burst transfers on the system bus 56 according to the PCI local bus specification, where a burst is comprised of multiple single transactions with implicit sequential addressing after the first transaction.

Accesses to the memory from the data port 80 also support direct memory access. Preferably, transfers on the data port 80 to or from the memory 72 employ pipelined transactions according to the AGP specification, where the transaction request, size, and address are supplied to the interface device 70 by the data transfer controller 68 over a set of sideband signals. Preferably, the graphic aperture (memory window) is at least 256 Mbytes. The data transfer is subsequently performed by the interface device 70 over the data port data bus in response to the request. Transaction requests can be made concurrently with data transfers using separate sideband data signals.

The memory 72 accepts data from or provides data to the CPU 74, the data transfer controller 68 and the system bus 82. The memory 72 comprises a synchronous DRAM (SDRAM) memory, such as a Texas Instruments' TMS 626162. Alternatively, a SDRAM-II, Double Data Rate SDRAM (DDR SDRAM), a sync-link DRAM (SL-DRAM), a RAMBUS DRAM (RDRAM), Direct RDRAM, Multi-Bank DRAM (MDRAM), Cache Enhanced SDRAM (ES-DRAM), or a non-synchronous memory is used. The memory 72 may comprise one or more memory components and one or more modules, such as three 32 Mbytes DIMM modules. Each memory component is associated with physical locations in the memory 72. Preferably, all of the memory components operatively connect to and are controlled by the interface device 70 (one memory). Less than all or other sources of control may be used. The memory port 76 of the interface device 70 comprises a memory port 96 of the memory. More than one memory port 96 may be used.

Figure 3:
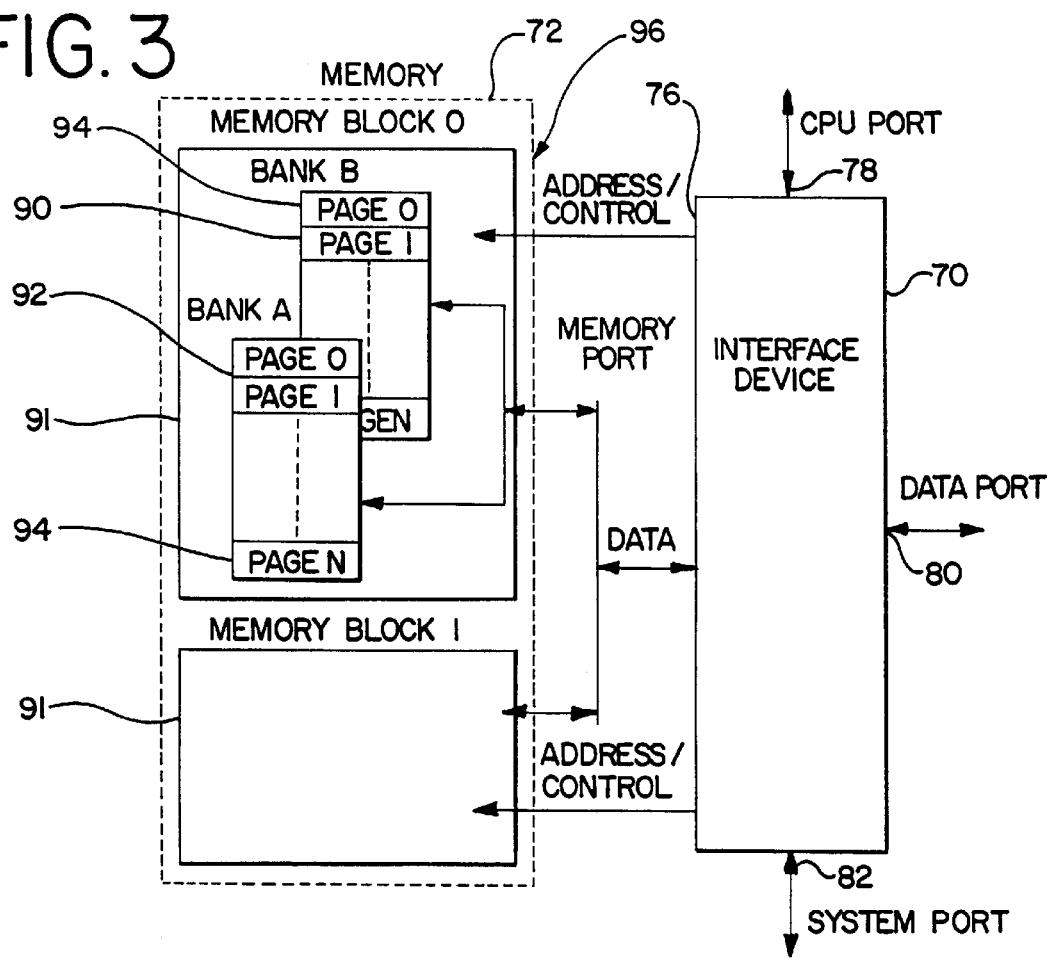
FIG. 3 is a block diagram of one embodiment of a memory and an interface device of FIG. 2.

Referring to FIG. 3, the memory preferably comprises two memory banks 90 and 92 in one or more blocks 91. More or fewer banks 90, 92 or blocks 91 may be used. Preferably, each bank 90, 92 comprises one or more pages 94.

Referring to FIG. 2, the memory 72 provides storage for CPU code and data, ultrasound image data from the data transfer controller 68, the CPU 74, or the system bus 56, and other data provided from the CPU 74, the data transfer controller 68, or the system bus 56. Other data may include text, graphics or control plane data for display, audio data, control and parameter data, messaging data, and patient information. Preferably, one area or section of the memory 72 is dedicated to CPU code and data and interprocessor communication and control data. As shown in FIG. 10, a 4 GB address range is used, but other ranges may be used. From 512 Kbytes to 1 Mbyte, legacy components (DOS compatibility) are located in the system addresses space. In FIG. 10, BIOS represents the system boot and configuration ROM occupying 128 kB within the 512 kB to 1 MB range and 1 MB at the top of the 4 GB address range. Resources connected to the system bus 56 are accessed in the 2 GB to 40 GB–20 MB range. Preferably, at least 64 Mbytes of memory is dedicated to acoustic, waveform, text and graphics, and video storage. Other memory allocations and maps may be used.

The CPU 74 is a programmable processor operable to run operating system, user interface, communication, control, applications and ultrasound data processing software or any sub-set of this software. Preferably, the CPU 74 is a 64 bit single instruction multiple data processor (SIMD), such as Intel's Pentium II® processor (e.g. 350 MHz with a 100 MHz frontside bus and 512 Kbytes of L2 cache integrated in a slot 1 single edge contact cartridge). As used herein, single instruction multiple data processors are processors capable of applying a single instruction on multiple data, such as in parallel processing paths. Furthermore, a multi-media extension (MMX) SIMD processor may be used. Other processors may be used, such as by other manufacturers, with 32 bits, or without SIMD capability.

Preferably, a cache memory is internal to and managed by the CPU 74, but in alternative embodiments the cache memory may reside on a host-bus, and be managed by the interface device 70. Other embodiments may contain both CPU internal cache and host bus cache which are managed by either the CPU 74, interface device 70, or both. The cache memory reduces transfers to memory 72 on the CPU port 78 and improves performance for instructions and data that are repeatedly used. The cache memory of the CPU 74 temporarily stores ultrasound data, such as image data, for processing by the CPU 74. Upon completion of the processing, the ultrasound data is stored in the memory 72. Additional ultrasound data is then stored in the cache of the CPU 74 for undergoing the same processing. Furthermore, the cache memory may contain both instructions for execution by the CPU 74 as well as ultrasound data, such as image data.

The host bus connects to the CPU port 78 of the interface device 70. The CPU 74, using the host bus, obtains software data (instruction code) from the memory 72 for execution. The CPU 74 operates or executes pursuant to the software data.

Figure 6:
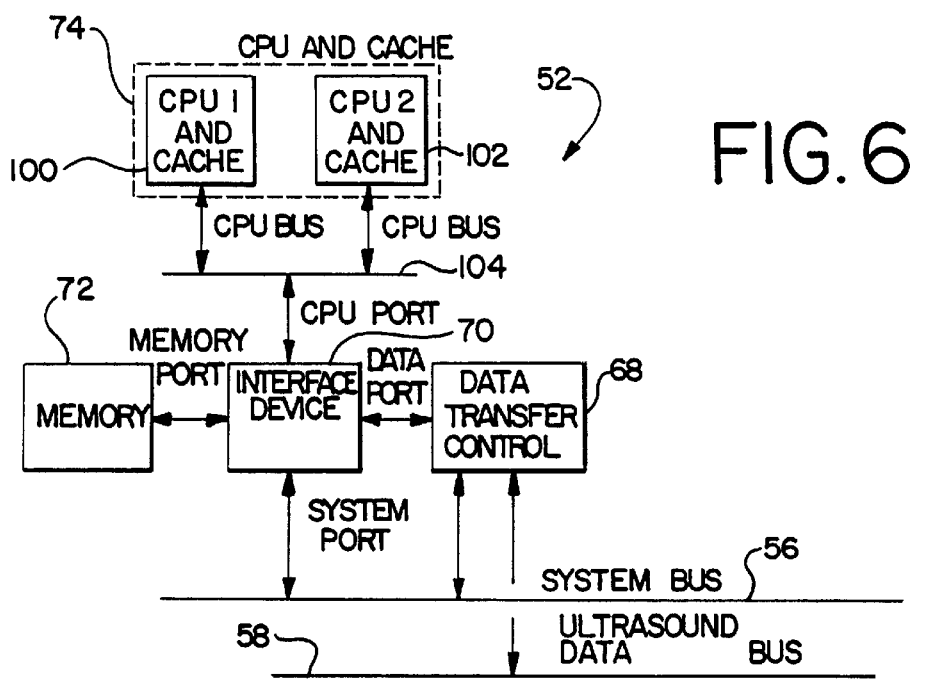
FIG. 6 is a block diagram of a multi-processor system for use in the data processing system of FIG. 1.

In an alternative embodiment, the CPU 74 comprises two or more microprocessors. Referring to FIG. 6, two symmetric processors 100 and 102 are shown. Preferably, the processors 100 and 102, such as Intel's Pentium® processors, operate pursuant to a symmetric multiprocessing protocol. For example, Intel's multiprocessor specification (version 1.4 May 1997) defines the use. Preferably, a master slave relationship or any other hierarchy or geometry limitations on processing and communications is not created between the processors 100 and 102. The processors 100 and 102 share the same memory space and access the memory 72 with the same addresses. This memory symmetry allows both processors 100, 102 to execute a single copy of the operating system (instruction code and data) stored in the memory 72. The processors 100 and 102 also share access to the same input and output subsystem, such as a CPU or host bus 104 and the associated input and output ports and interrupt controllers. This input/output symmetry allows either processor 100 and 102 to receive interrupts from any other component of the system 52. Other types of symmetry pursuant to the same or different multi processing protocols may be used. For example, memory symmetry, but not I/O symmetry may be employed.

Referring to FIG. 2, the CPU 74 initiates transfers on the system bus 56 through the interface device 70. Preferably, the system bus 56 is a high performance multi-master bus, such as a PCI local bus (revision 2.1 or later) with Industrial Computer Mfg. Group Compact PCI (revision 2.0) mechanical components and connector technologies. The system bus 56 may comprise other multi-master or non-multi-master buses. The system bus 56 provides a data path for the transfer of communication, control, parameter and other information between any master or initiator and any slave or target resource connected to the system bus 56. The system bus 56 also transfers other data, such as patient, ultrasound data and instruction code data, to the memory 72. Preferably, any transfer of data on the system bus 56 targeted for storage in the memory 72 passes through the system port 70. Alternatively, the data passes through the data port 80.

The system port 82 of the interface device 70 preferably includes system bus arbitration and control logic. Preferably, the system port 82, the peripheral interfaces 66, ultrasound acoustic acquisition path 60, the video/audio acquisition path 62, video/audio reconstruction path 64 and the beamformer 24 are operable to act as the master/slave or both master and slave resources on the system bus 56. Preferably, the CPU 74 is capable of locking (uninterrupted multitransfers) the memory 72 pursuant to the PCI specification, but other resources may use other means for assuring proper operation when accessed by multiple bus masters. Other connections between the system bus 56 and other resources of the data processing system 26 or peripherals may be provided.

Control, communication and parameter data is formatted as appropriate for its purpose. Other control data includes reset signals for processors, boards and the system 50 distributed under the control of the CPU 74. Furthermore, timing information (e.g. VCR annotation (counter) update data), and interrupt data (e.g. to identify frames of display data, physio triggers, vertical blanks, and power failure) is managed by the CPU 74.

Local mailbox memories, such as 64 K×32 memories, may be provided as local resources in the paths connected to the system bus 56 for temporarily storing communication, control and parameter data. Preferably, interprocessor communications are buffered in the memory 72 and employ either point-to-point dedicated communications or common resources with software arbitration, but alternatively may employ only the mailbox memory or a combination of the memory 72 and the local mailbox memory for interprocessor communication.

The peripheral interfaces 66 allow communication and transfer of data from any of the various peripherals to the system bus 56. For a block diagram of the peripheral interfaces 66, see the attached Appendix C and FIG. 13. The south bridge of Appendix C and FIG. 13 preferably comprises an Intel 82371 AB (PIIX4 or X6). The peripheral interfaces 66, such as the south bridge, may perform subtractive decode for any transactions below 16 Mbytes on the system bus 56 pursuant to the PCI bus specification.

Preferably, the peripheral interfaces 66 comprise one or more industry standard interfaces, such as an RS-232 serial interface, an IEEE Std. 1394-1995 (Firewire) interface, a Universal Serial Bus (USB) interface or an Ethernet 10/100 base T interface. Preferably, one or more high bandwidth Firewire interfaces connect to any hard disk drives 28, removable media devices 30 or other peripherals supporting the Firewire standard, such as a digital VCR. Furthermore, the Firewire interface may connect to the video/audio acquisition data path 62 for direct transfers of digital video data. Preferably, the Firewire interface includes an Open Host Controller Interface Specification compatible device.

One or more lower bandwidth USB interfaces connect to any physio modules 38, user interfaces 42, and other peripherals supporting the USB standard, such as printers and cameras. Preferably, the USB interfaces include a controller compatible with the Universal Host Controller Interface guidelines. Using a USB interface, the physiological or patient data acquired in real time from the physio module peripheral 38 is transferred over the system bus 56 for storage in the memory 72.

One or more 10/100 Base-T Ethernet interfaces, such as AMD's AM 79C973 10/100 Mb PCI interface Ethernet controller with integrated physical layer interfaces, connect to one or more computers or networks, such as the LAN 32. Preferably, the Ethernet interface directly connects to the system bus 56 for direct memory access burst transfers to or from the memory 72. LED's are preferably provided to indicate the Ethernet interface status. A standard RJ45 connector is provided for the LAN 32 connection, but other LAN 32 connections may be used.

Information from any of the various other peripherals is transferred through the peripheral interfaces 66 to the system bus 56. By using standardized interfaces, the number of distinct interfaces required in the system is reduced and may facilitate testing of the data processing system 52 through the peripheral interfaces 66. Furthermore, JTAG, and I²C serial busses or other busses are connected to various resources or boards to facilitate testing, system monitoring (temperature), and board level identification and control.

Figure 7:
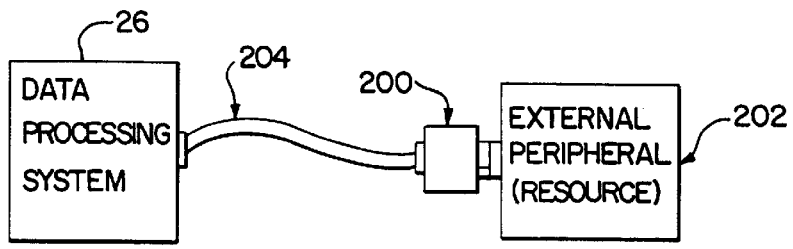
FIG. 7 is a block diagram of a peripheral connection.

As an alternative, the peripheral interfaces 66 include one or more non-standard interfaces. As an alternative to non-standard interfaces, adapter modules as shown in FIG. 7 at 200 are used. Depending on the non-standard data and physical interface of any external peripheral 202, the physical plugs and circuitry of the adaptor module are configured to allow connectivity and the transfer of data.

The adaptor module 200 is shown connected between an external peripheral 202 and the data processing system 26. Preferably, the adaptor module 200 connects directly to the external peripheral 202 and connects to the data processing system 26 through a standard communication interface cable 204. In alternative embodiments, a cable is provided between the adaptor module 200 and the external peripheral 202, and the adaptor module 200 connects directly or through another cable to the data processing system 26. The external peripheral 202 includes one or more peripheral devices, including any of the peripherals discussed above.

The adaptor module 200 is preferably powered by the peripheral interface 66 (see FIG. 2) of the data processing system 26, such as a Firewire or USB interface. The IEEE Std. 1394-1995 (Firewire) (e.g. 8–40 volts at 1.5 amps per port) and USB (e.g. 5 volts±5% at 500 mAmps per port) serial buses and associated interfaces include provisions for powering external devices. Preferably, three Firewire and two USB ports are used, and current limited, such as with resetable overcurrent protection.

The adaptor module 20 preferably connects to non-standard physical plugs associated with the external peripheral 202 and performs communication, control, data, and interface signal translation to or from the external peripheral 202. For example, data from a non-standard video page printer is translated to conform with the standard Firewire or USB interface. Likewise information provided from the data processing system 26 to the external peripheral 202 is translated for use by the external peripheral 202.

Other than the system bus 56 and peripheral interfaces 66, the ultrasound data bus 58 comprises a data path for transferring ultrasound data between any of various paths and the memory 72. Preferably, the ultrasound data bus 58 is a 32 bit synchronous bus operating at 48 MHz and allowing 48 requesters. In one embodiment, the maximum, minimum and granularity of data packets on the data bus 58 is 1024, 256 and 16 bytes, respectively, but other values may be used. The ultrasound data bus 58 preferably comprises separate transfer request and data transfer signal lines and any request has a maximum latency of 10 µsec. This separation permits requests for transfer to be performed independently from and overlapped with actual transfers of ultrasound data. Preferably, the bandwidth of the bus is approximately 160 Mbytes (192 Mbytes/sec with 85% efficiency) and is distributed for various data (e.g. in Mbytes/sec: B/M-mode-12, F-mode-6.67, D-mode-0.28, full video image capture-8, full video review-32, ¼ size review-8, VCR playback-24, Image reconstruction-24 to 32, Text, graphics and display field control reconstruction-36 and physio/derived waveform/audio reconstruction-0.25). Distribution is preferably maintained through uniformly distributed requests. Other data buses may be used, including buses configured for different numbers of requesters, clocks, bit widths, and request latencies.

Figure 8:
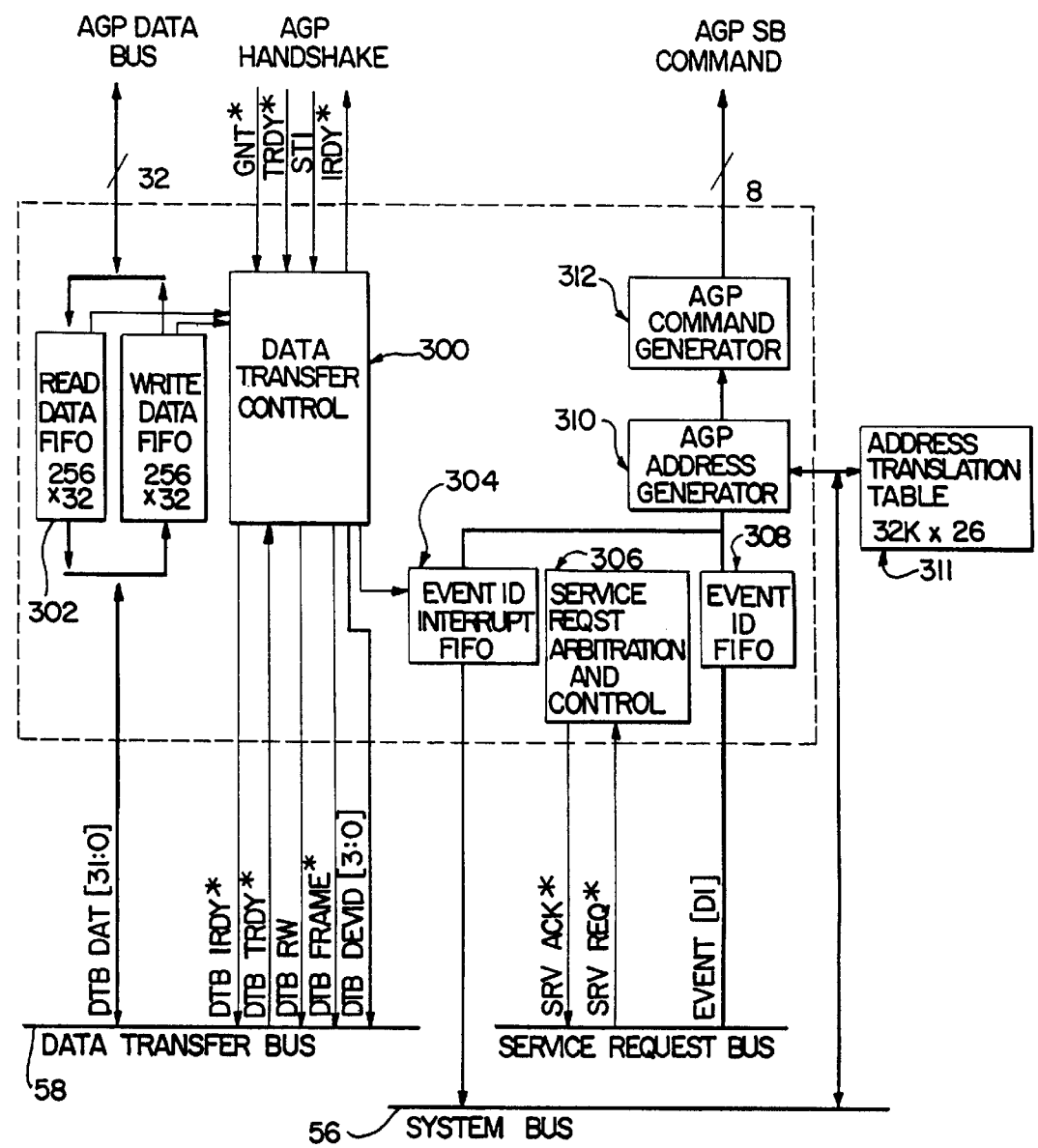
FIG. 8 is a block diagram of one embodiment of a data transfer controller of FIG. 2.
Figure 11:
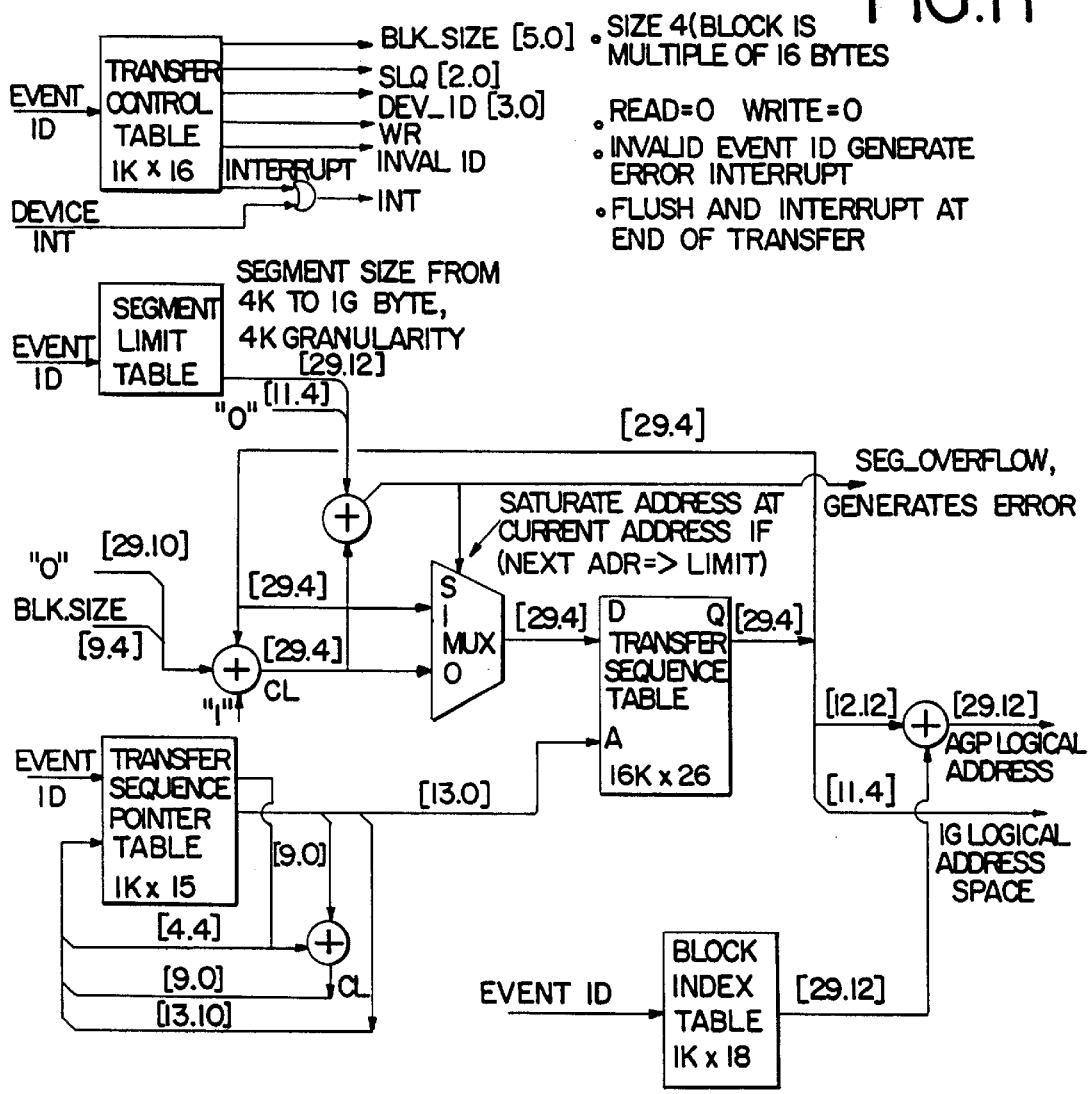
FIG. 11 is a block logic diagram of one preferred embodiment for address generation.
Figure 12:
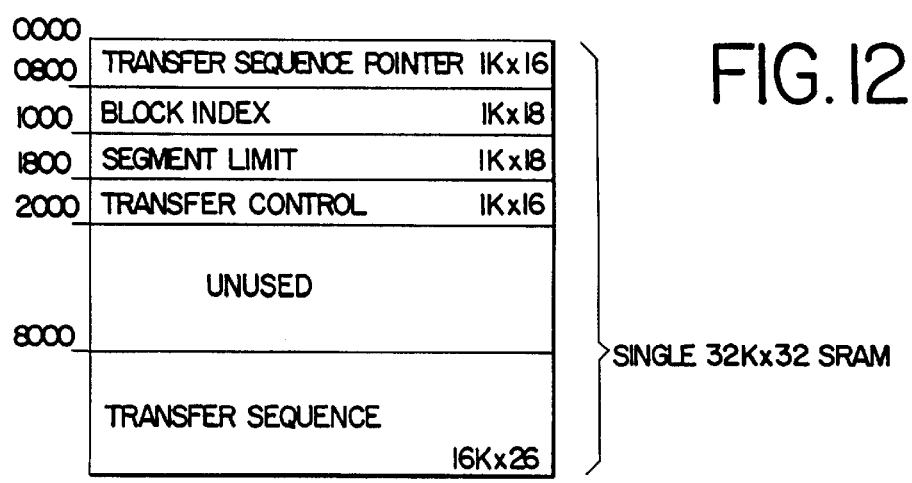
FIG. 12 is a representative memory map for an address generator table of one preferred embodiment.

An ultrasound data path may include the data transfer controller 68. Referring to FIG. 8, the data transfer controller 68 preferably includes a controller 300, read and write buffers 302, an interrupt buffer 304, a service controller 306, an Event ID buffer 308, an address generator 310, and a AGP command generator 312. To transfer data, an event ID is stored in the event ID buffer 308 (FIFO) when a request for transfer is made. The control 300 uses the event ID to access transfer control parameters, including generation of logical addresses. FIG. 11 shows a logical diagram for address generation as discussed above and FIG. 12 and appendix B show an associated memory map for an address generator table 311. Preferably, address generation is done in parallel (address generation for the next event is done during data transfer for the current event).

The address generator 310 generates the logical addresses based on the control parameters. The results are provided to the AGP command generator 312. The AGP logical address is generated by a sequential process of table reads and computations. The 30-bit AGP logical address (1 Gbyte) consists of an 18-bit segment address and the remaining 12 bits point to a location within a 4 Kbyte segment. The 18-bit logical segment address is computed by adding a memory Block Index pointer for the event ID to the output of the address table. Additionally, the address table output is added to the block size to compute the base address for the next transfer for the event ID. This allows successive block sequential transfers to access main memory 72 in a logically contiguous address space while using the same event ID.

For block non-sequential transfers, the address table is not rewritten. The amount of data is determined for generating the next sequential address. After each block non-sequential transfer, the 10 least significant bits are incremented to generate a new address table address, allowing subsequent transfers with the same event ID to access main memory 72 in a non-contiguous manner within the selected segment.

The AGP command generator 312 requests transfer to or from the main memory 72 over an AGP sideband command bus and tracks the interface device 70 to prevent overflow. The sideband command bus, as specified in Intel's AGP specification, demultiplexes the address and data busses. Preferably, the command requests correspond to 16 byte transfers, but other sizes may be used.

The read or write buffer 302, such as 256×32 FIFOs, transfer the data under control of the controller 300 and convert data rates (e.g. from the 64 MHz data port 80 to the 48 MHz data bus 58). After completion of a transfer, the AGP command generator 312 sends a FLUSH request to the interface device 70 to insure any remaining data buffered in the interface device 70 is sent to memory 72. Upon acknowledgement of a complete transfer, the controller 300 writes the event ID into the interrupt buffer 304. The CPU 74 is interrupted to indicate the availability of the data.

The service controller 306 arbitrates between requests for transfer and enables the requesting path to send the event ID and any other information associated with the transfer request to the controller 3000.

Referring to FIG. 2, the data transfer controller 68 performs arbitration and data buffering, data flow control, data reformatting or repacketizing, protocol and interface signal translation, and packet starting address generation. The data transfer controller 68 is a source of or provides ultrasound data to various components of the system 50. Preferably, the data transfer controller 68 time interleaves burst transfers of packets of ultrasound data between the memory 72 and any of the ultrasound data processing paths, such as the ultrasound acoustic data acquisition path 60, the video/audio acquisition path 62 and the video/audio reconstruction path 64.

The data transfer controller 68 buffers ultrasound data transferred to the memory 72 based on various requirements of the data processing system 52. Both the data transfer controller 68 and the interface device 70 include buffers. The interface device 70 queues or buffers data to minimize latency, maximize bandwidth and support concurrence of transfers on each port of the interface device 70. The buffers preferably include dedicated write buffers and read buffers, but other buffer structures, such as one buffer for both read and write operations, may be used. To maximize transfer efficiency, the data transfer controller 68 transfers only ultrasound data (PCI or control commands transfer, as specified by the AGP specification, are not supported, but may be in other embodiments). Other transfer schemes may be used.

Buffering is also performed in the paths interfacing to the ultrasound data bus 58. The size of any buffer to prevent the loss of data is based on data path bandwidth and maximum transfer latency. For example, the sum of the ultrasound data bandwidth requirements of the ultrasound acoustic data acquisition path 60, the video/audio acquisition path 62, and the video/audio reconstruction path 64 is less than the sustainable bandwidth supported by the interface device 70 between the data port 80 and the memory port 76. The memory 72 bandwidth sustainable by the interface device 70 preferably includes time or bandwidth required for concurrent transfers between the CPU port 78 and the memory port 76, and the system port 82 and the memory port 76. Buffering by the interface device 70 allows for latency of any real-time transfer of ultrasound data while control or other data is transferred through the interface device 70 and allows more efficient burst transfers between ports. Buffering by the data transfer controller 68 allows for latency of data transfers on the data port 80 permits repackatizing and isolates clock domains between the data port 80 and the ultrasound data bus 58. Local buffers in the paths connected to the ultrasound data bus 58 absorb bus latency and the size of local buffers may be determined as follows:

Minimum buffer size (bytes)=local data rate (Mbytes/sec)×transfer latency ($\mu$sec)

Preferably, the maximum transfer latency is 100 $\mu$sec, but other latencies may be used.

When considering concurrent operation of all the ports of the interface device 70 and data transfers to the memory 72, the bandwidth of the memory port 76 may be the limiting factor and may require trade-offs between the bandwidth requirements for the CPU port 78, data port 80, and the system port 82. Increasing the bandwidth of the memory 72 through the use of higher clock rates, wider data widths or more efficient transfers permits higher concurrent bandwidths on the other ports of the interface device 70 for transfers to the memory 72.

Preferably, the data transfers between the data port 80 of the interface device 70 and memory 72 are non-coherent (i.e. cache memory on the CPU port of the interface 70 is not accessed or any cache status updated as part of the data transfer). Non-coherent transfers eliminate potential performance degradation resulting from coherency testing (snooping) of each transfer. Preferably, software is provided for maintaining the coherency between the cache memory and the memory 72 to ensure that valid data is used during data processing and placed in the memory 72 after data processing. Thus, the CPU 72 establishes coherency as part of its data processing operation. In alternative embodiments, the CPU 74 uses the memory 72 for processing the ultrasound image data without using the cache memory, or snooping may occur during transfers on the data port 80 to or from memory 72. Preferably, coherency between the cache memory of the CPU 74 and the memory 72 is maintained for transfers of data, such as control information, ultrasound data, and patient information, to or from the memory 72 through the system port 82, and to or from main memory 72 through the CPU port 78.

Various devices comprising sources of ultrasound data, such as in the ultrasound acoustic data acquisition path 60, the video/audio acquisition data path 62 and the video/audio reconstruction path 64, are described below as an example. Any device capable of providing the type of ultrasound data may be used. Likewise, any device capable of receiving appropriate control instructions may be used. The format of the data (image, audio, control or other) provided to or from the device is consistent with the format of the appropriate other devices of the system 50.

Figure 4:
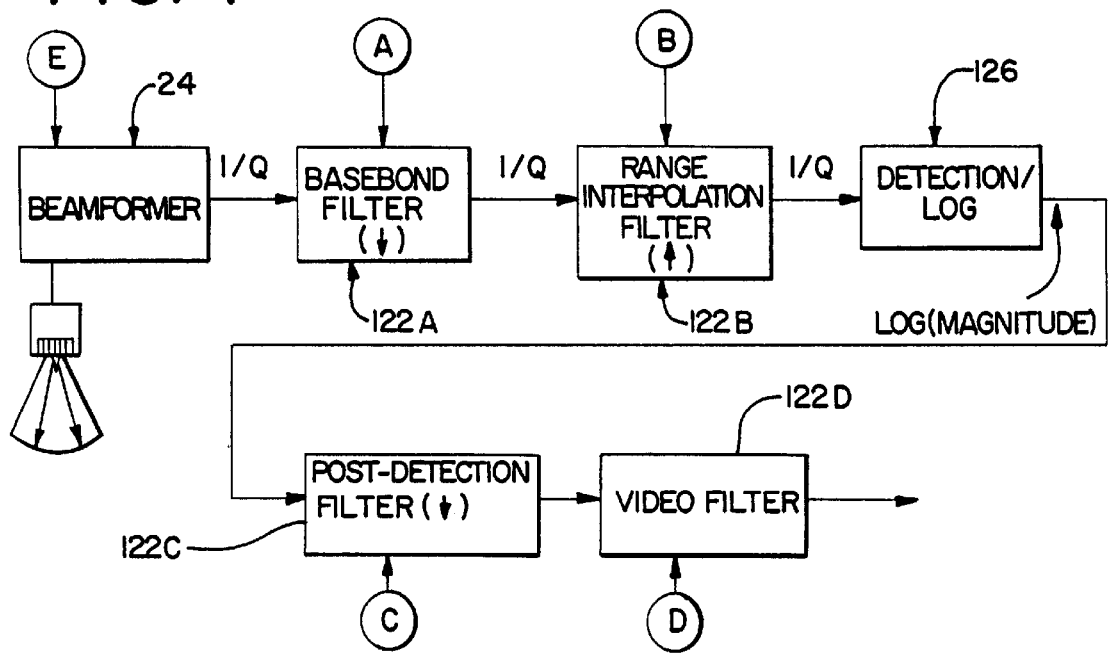
FIG. 4 is a block diagram of one embodiment of an ultrasound acoustic data acquisition path of FIG. 2.

One source of ultrasound data for processing is the ultrasound acoustic data acquisition path 60. Referring to FIG. 4, an ultrasound acoustic data acquisition path for B/M-mode is shown at 120. The acquisition data path 120 includes one or more filters 122A–D, a log compression and detection circuit 126. Additional components may be included. Any of the filters 122A–D and the log compression and detection circuit 126 may be implemented with a digital signal processor or other hardware. The acquisition data path 120 receives information from the beamformer 24, such as, complex baseband ultrasound image data. The acquisition data path 120 performs analytic, detection and other post-detection processing to generate one or more of B-mode or M-mode information. The acquisition data path 120 may comprise the data path disclosed in U.S. application Ser. No. 08/760,083 for an Ultrasonic Diagnostic Imaging System With Programmable Acoustic Signal Processor, filed Dec. 4, 1996 ('the 083 application). See also U.S. Pat. Nos. 5,623,930, 5,642,732, 5,285,788, 5,165,413, and 5,014,710. Preferably, the acquisition data path 120 is capable of generating detected B-mode data, M-mode data, color Doppler unfiltered energy, filtered energy, velocity and variance data and spectral Doppler data (derived waveform, spectrum and audio).

The processing carried out by the acquisition data path 120 and the beamformer 24 are connected to the system bus 56 for receiving control information from the CPU 74. The control information is either routed from the CPU port 78 to the system port 82 or from the memory 72 to the system port 82. The control information includes filter parameters, input controlling the selection of parameters (filter, Doppler or others), and other inputs controlling processing.

The control instructions preferably control the range grid for display. Complex baseband signals sampled on an initial range grid from the beamformer 24 are supplied as input data to a baseband filter 122A. In general, the baseband filter 122A performs harmonic (or fundamental) noise suppression filtering in the range dimension on the complex baseband signals from the beamformer 24, and provides selectable sampling rate decimation in range by a factor of L/M. Preferably, the bandwidth of the baseband filter 122A is adjusted as a function of the selected ratio L/M to band limit the signal prior to decimation and to prevent aliasing, as is well known in the art.

The baseband filter 122A supplies band limited and resampled complex baseband data to a range interpolation filter 122B. The range interpolation filter 122B performs up-sampling in range prior to nonlinear detection and log processing. The range filter 122B performs up-sampling by a factor of R/S. The decimation factor L/M and the interpolation factor R/S are preferably selected as a function of a number of parameters, including the size of the image to be displayed, the transmit center frequency, the number of samples to be displayed, and the number of beams. In this embodiment, decimation by the baseband filter 122A (L/M<1) is never employed in conjunction with range interpolation by the range interpolation filter 122B (R/S>1). In alternative embodiments, the baseband filter 122A and range filter 122B may be combined into a common block which implements both the L/M and the R/S resampling selections.

The output samples generated by the range interpolation filter 122B are supplied to a detection stage 126, which performs magnitude detection and log compression on each data sample. The data samples supplied by the range interpolation filter 122B are on an intermediate range grid, which is equal to the initial range grid of the beamformer stage 24 modified by the factor (L/M)×(R/S). The detection stage 126 output is supplied to a post-detection filter 122C. The post-detection filter 122C performs sample rate decimation by a factor of 1 (no decimation) or ½. When decimation by ½ is selected, filtering or band limiting of the magnitude samples is performed prior to decimation to a final range grid. This is done to substantially prevent aliasing.

The intermediate range grid on which data is supplied to the detection stage 126 is preferably sufficiently fine (sampled at a high enough rate) to prevent aliasing due to spectral broadening which occurs through the nonlinear processing operations performed in the detection stage 126. The range grid required prior to nonlinear processing to prevent aliasing will be dependent on the overall bandwidth of the signal from the beamformer stage 24 and the frequency response employed in the baseband filter 122A. In general, as the final range grid value increases as described below, it is preferable to employ an intermediate range grid that is finer than the final range grid (more highly over sampled) and then to band limit and decimate down to the final range grid after nonlinear processing in the detection stage 126, to preserve information content and to prevent aliasing artifacts. For smaller values of the final range grid, the final range grid may be fine enough to sufficiently over sample the signal prior to nonlinear processing, in this way avoiding the need for increased over-sampling prior to nonlinear processing and subsequent band limiting and decimation after nonlinear processing.

Output samples from the post-detection filter 122C are sampled on the final range grid, and are supplied to a video filter 122D. The video filter 122D performs final shaping of the spectrum of the signal prior to scan conversion and display. The video filter 122D is programmable, and may be set to pass-through mode where no filtering operation is performed, or may be employed to perform further band limiting or band peaking (edge enhancement) on the range data.

Other acquisition data paths 120 may be used, such as with different filter structures or processes, including post detection variable filtering. For example, the systems disclosed with respect to FIGS. 1, 17 or 18 of the '083 application or other systems may be used. Furthermore, different components may be used, such as analog or digital.

Referring to FIG. 2 and in the preferred embodiment, the ultrasound acoustic data acquisition path 60 provides processing for various modalities, and provides direct acquisition and transfer of beamformer acoustic data. B-mode and M-mode data output by the ultrasound acoustic data acquisition path 60 consists of 8 bit samples of magnitude detected and log compressed acoustic data. Spectral Doppler data output from the ultrasound acoustic data acquisition path 60 consists of 8 bit spectral magnitude (128 point per spectrum), 16 bit of each of forward and reverse (left and right) audio, and 16 bits for each (e.g. such as 4 waveforms) of the derived waveform data. Doppler Tissue and Color Doppler data output from the ultrasound acoustic data acquisition path 60 consists of 8 bits of each of unfiltered energy, energy, velocity (signed) and variance. Beamformer complex acoustic data (pre-detection) output from the ultrasound acoustic data acquisition path 60 consists of 16 bits of each of I and Q data. Data output from the ultrasound acoustic data acquisition path 60 is generally packed in 32 bit words and grouped in packets representing an acoustic line, group, or specific interval of time. In alternative embodiments, other data types, formatting, packing and grouping may be employed.

The output from the ultrasound acoustic data acquisition path 60 is stored in the memory 72. In alternative embodiments, additional data may be stored in the memory 72 from the ultrasound acoustic data acquisition path 60, such as transducer positional information, or any data received from the beamformer 24.

Another ultrasound data path or portion of a data path is the video/audio acquisition path 62. The video/audio acquisition path 62 receives digital video or audio data from the video/audio reconstruction path 64 and analog video/audio data from the analog video/audio device 54. Additional sources of digital or analog video/audio data may be provided. The video information generally comprises ultrasound image data. Compressed or uncompressed video data stored in the memory 72 is formatted as 8 bits for each color component. The video information may be in YUV 4:4:4, YUV 4:2:2, Y only, or RGB color spaces or any alternative color space and component sub-sampling. Preferably, YUV 4:2:2 data is stored in the memory 72 as two files, such as one file of progressive Y and a second file of U/V interleaved data. Alternatively, a four file format of Y and U/V component interleaved planes for even and odd field (such as for VCR playback) or other formats are used. The video/audio acquisition path 62 performs analog to digital and digital to analog conversion. Digital video or audio information is output to the ultrasound data bus 58 for storage in the memory 72 and any subsequent processing by the CPU 74. Data from the video/audio reconstruction path 64 is input to the video/audio acquisition data path 62 for analog video standards conversion and output to the analog video/audio device 54.

The video/audio acquisition path 62 preferably also performs real time video compression and decompression. The video/audio acquisition path 62 may perform fewer, additional or different functions. The video/audio acquisition path 62 preferably compresses and decompresses using the Joint Photographics Expert Group (JPEG) compression standard (ISO 10918 Draft International Standard) or other standards. Prior to compression, the video ultrasound data may be minified or scaled to further reduce the amount of information for storage. Any compressed video ultrasound data stored in the memory 72 may be transferred to the video/audio acquisition data path 62 over the ultrasound data bus 58 for decompression or transferred over the system bus 56 to an external peripheral. Decompressed ultrasound data is saved in the memory 72 and then transferred to the video/audio reconstruction data path 64 for reconstruction and output.

The video/audio acquisition path 62 preferably also supports static video frame capture of digital video data from the video/audio reconstruction path 64, and subsequent transfer to the memory 72. The CPU 74 may then compress the video data using either lossless or lossy compression algorithms. Compressed data stored in the memory 72 may be decompressed by the CPU 74.

Figure 5:
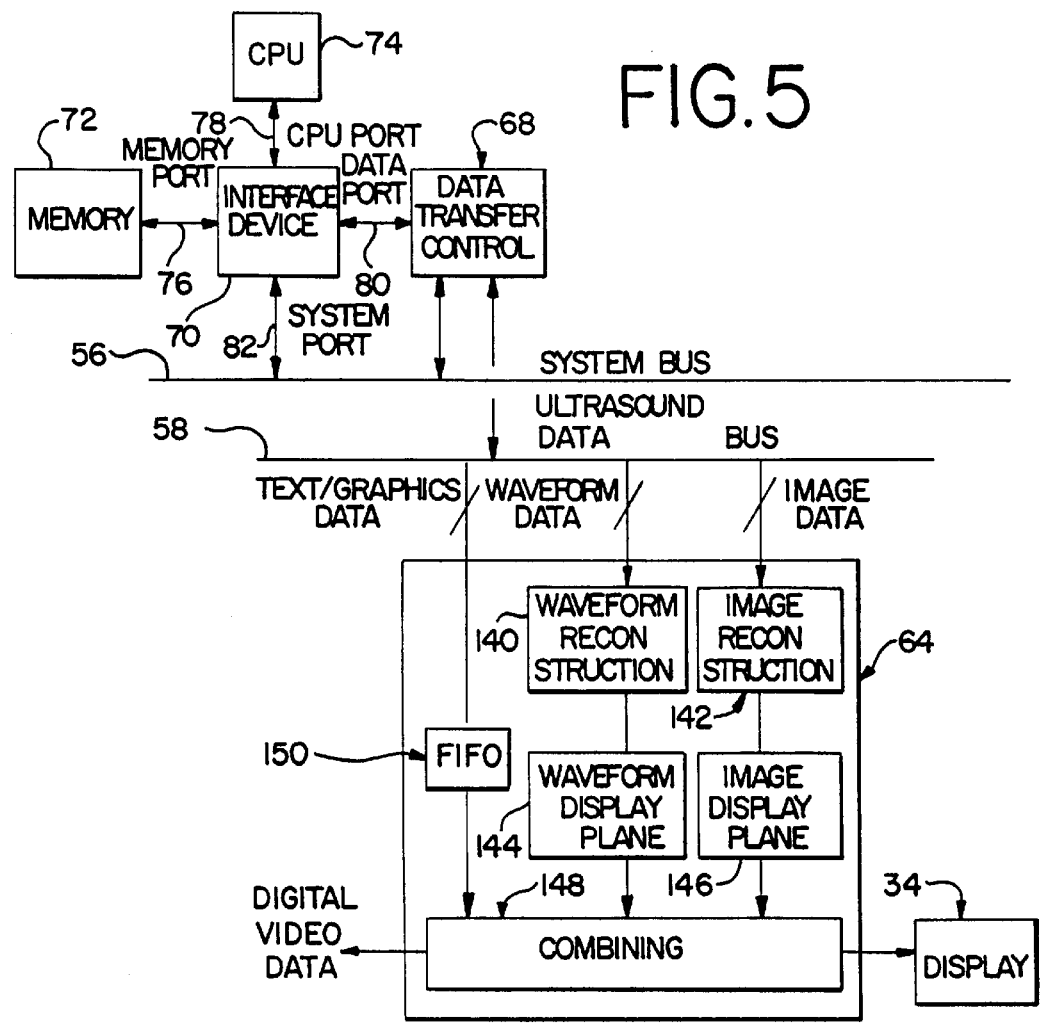
FIG. 5 is a block diagram of one embodiment of a portion of the data processing system of FIG. 2, including a video reconstruction data path.

Another ultrasound data path or portion of a data path is the video/audio reconstruction path 64. Referring to FIG. 5, the video/audio reconstruction path 64 comprises waveform and image reconstruction circuitry 140 and 142, waveform and image display plane memories 144 and 146, and combining circuitry 148. As another example, U.S. Pat. Nos. 5,563,810 and 5,479,926 discuss reconstruction processing and structures. The video/audio reconstruction path 64 receives text and graphics plane data, waveform data, and ultrasound data (decompressed video, B-mode acoustic, M-mode acoustic, color Doppler acoustic, spectral Doppler or other types of data) to be used in constructing an image for display. The ultrasound data is combined with the waveform data and the text and graphics plane data and output to a display 34, the video/audio acquisition path 62 or other outputs.

The image reconstruction circuitry 142 receives the ultrasound image data. The image reconstruction circuitry 142 comprises various processing stages for performing enhanced contrast resolution imaging, color Doppler frame interpolation, automatic area measurement processing, color mapping, or other processes. For example, see U.S. Pat. No. 5,479,926 to Ustuner et al. Other processes may include decompression or other operations optimally performed after bulk storage and prior to image reconstruction and display. The image reconstruction circuitry 142 performs scan conversion or spatial transformation and resampling operations to map data received on an acoustic grid or other grid to a display grid. For example, the processing disclosed in U.S. Pat. No. 5,563,810 for a Device And Method For Performing Acoustic Scan Conversion is used. The reconstructed ultrasound image data is stored in the image display plane memory 146.

The waveform data, including spectral Doppler derived waveform data and physiological waveform data is reconstructed or formatted for display by the waveform reconstruction circuitry 140. The reconstructed waveform information is stored in the waveform display plane memory 144.

Text and graphics plane data, such as non-scrolling data is passed through a queue 150 to the combining circuitry 148. Preferably, the text and graphics plane data is generated by the CPU 74 and stored in the memory 72. For example, the CPU 74 uses the ultrasound data or any other data, such as physiological data, to calculate quantities. The quantities are stored in the memory 72 as data or textual information, along with calipers or other graphic information. Multiple frames of text and graphics plane data are preferably stored in the memory 72 and selected by changing an address pointer.

Plane data, such as text and graphics plane data, is data stored uncombined with other types of data. For example, combined data is video data including text and image information. Text and graphics plane data is output to or within the video/audio reconstruction path 64 for combining with other types of data. Typically, plane data is output for combination at a rate corresponding to an update rate of the receiving device, such as the display 34. The text and graphics plane data is output from the memory 72 or another source at a rate that is substantially the same as an update or refresh rate of display 34. Due to the other potential bandwidth requirements of the memory port 76, the queue 150, such as a 1 k×32 first-in, first-out buffer, absorbs any latency in receiving the text and graphics plane data. Thus, the memory 72 outputs the text and graphics plane data at substantially the same but varying rate as the refresh rate of the display 34. The first-in, first-out text queue 150 acts to output without variation the text and graphics plane data at substantially the same rate as the refresh rate of the display 34. Preferably, the text and graphics data is converted to RGB values with a look-up table prior to combination.

The text queue 150, the waveform display plane memory 144, and the image display plane memory 146 output data at substantially the refresh or update rate of the display 34 to the combiner 148. The combining circuitry generates composite ultrasound video data. The ultrasound video data is converted to analog and displayed on the monitor or display 34. The display 34 comprises a CRT or flat panel device.

The video/audio reconstruction data path 64 receives control plane data from the memory 72. Preferably, the control plane data comprises 4 bits/pixel for each black-and-white and color pixel, but other data formats may be used. The control plane data is stored in a 1 K×32 FIFO buffer for subsequent use. The control plane data provides control information for the processing and combination of data, such as color or black-and-white look up table palette selection, identification of scrolling regions, strip or waveform identification, threshold map selection (programmable thresholds), black-and-white/color combining selections, image mask selection (clipping), and blanking background color (user selected). Preferably, the control plane data is transferred over the ultrasound data bus 58 and output from the memory 72 at a rate corresponding to the refresh rate of the display 34.

Spectral Doppler audio, microphone (or other external audio information), and physiological audio (phono physio) data is also transferred from the memory 72 or another source to the video/audio reconstruction data path 64. The various audio data is re-sampled and combined or mixed to generate a composite audio output. The audio information is output to the speakers 36, transferred to the memory 74, for storage, or output to another peripheral.

The system described above allows for flexible processing of ultrasound data and flexible control of processing. The CPU 74 controls the system 50 and performs ultrasound data processing. The memory 72 stores instruction code for the operation of the CPU 74, ultrasound data, control data, text and graphics data, and other data. The interface device 70 allows for efficient access between the CPU 74, the memory 72, various system data paths through the system port 82, and various ultrasound data paths through the data port 80.

II. Operation:

Referring to FIG. 9, a flow chart of the operation of the CPU 74 (FIG. 2) is shown at 400. The CPU 74 first initializes the system as represented by block 402. For example, various system checks are performed, and components (e.g. PCI compliant devices connected to the system bus 56) are configured for operation. Further operation of the CPU 74 is preferably performed in a multi-tasking environment. The various operations or functions are time interleaved. For example, the processing associated with two or more of a peripheral operation block 404, a memory management processing block 406, a user interface and other control processing block 408, a data processing block 410, and an application processing block 412 is interleaved. Preferably, the amount of time dedicated to each operation is dynamically based on the type of operation, the time of any request for the operation, and any other priority information.

An example of the processing associated with each block 404, 406, 408, 410 and 412 is discussed below with reference to FIGS. 2 and 9. Other organizations of flow may be used, such as additional or fewer processing tasks. Furthermore, different, more or less processing may be performed for each block 404, 406, 408, 410 and 412.

Upon power up, the CPU 74 executes from a non-volatile memory, such as an EEPROM, containing initial boot code. The boot code loads additional code from disk or LAN into the memory 72 for the CPU 74 to execute. The CPU 74 accesses the memory 72 through the interface device 70. Pursuant to the instruction code data, the CPU 74 controls operation of various components of the system 50.

The CPU 74 configures the interface device 70 and the peripheral interfaces 66 to communicate with peripherals, such as the user interface 42 or the local area network 32 (block 402 of FIG. 9). Information from a peripheral device is transferred on the system bus 56 to the memory 72 through the system port 82 and memory port 76. Alternatively or additionally, the information is provided to the CPU 74. The information may include new instruction code and data transferred from disk or system 50 mode selection data from the user interface. For example, the user selects B-mode or other operating modality, specific processing options, or other system operating modes. Other data may be downloaded through the peripheral interface to the memory 72 (block 404 of FIG. 9).

For a user selected mode of operation, the CPU 74 provides control instructions to the beamformer 24, the ultrasound data acquisition path 60, the video/audio acquisition path 62, the video/audio reconstruction data path 64, any peripherals (e.g. physio module or analog video/audio device 54) or combinations thereof over the system bus 56 (blocks 404 and 408 of FIG. 9). The control information designates operating modality, scan format, scan region, focus, gain, other beamformer controls (e.g. imaging parameters) and other settings selected by the user or predefined for the mode of operation. Different types of control information may be used, such as filtering parameters, scaling parameters and other information usable by one or more of the various data paths. Predefined settings for a particular mode of operation are stored in the memory 72, and may be changed or loaded from various peripherals, such as the LAN 32, the removable media device 30, or the hard disk drive 28. The control instructions may be provided from the memory 72 to the system port 82. Likewise, interprocessor communications are stored in the memory 72 and then provided to appropriate processors.

The control instructions provided by the CPU 74 depend upon the type of ultrasound data processing selected by the user. For example, the user may select to acquire ultrasound data from the ultrasound acoustic data acquisition path 60, or the video/audio acquisition data path 62. For the ultrasound acoustic data acquisition path 60, the CPU 74 sends control and parameter information to initialize or otherwise configure the various components in the ultrasound acoustic data acquisition path 60 and the beamformer 24. For acquiring ultrasound data from the video/audio acquisition data path 62, the CPU 74 sends control and parameter information to initialize or otherwise configure the video/audio acquisition data path 62. For example, the video/audio acquisition data path 62 is configured to receive analog or digital video and audio information and to compress or decompress the information.

In preparation for transferring acquired ultrasound data over the ultrasound data bus 58 to the memory 72, the CPU 74 also initializes or configures the data transfer controller 68 (block 402 of FIG. 9). The CPU 74 dynamically manages the data transfer controller 68 during real time operation of the system. The data transfer controller 68 receives the CPU 74 control data from the system bus 56. The CPU 74 initializes the data transfer controller 78 for the type of transfer (i.e. read or write) and the starting logical address associated with the ultrasound data. The assigned event ID corresponds to the transfer type and the starting logical address of the allocated memory block. The event ID also identifies packet size, interrupts, routing and other control information.

The event ID is generated by the CPU 74 in response to a request from the beamformer 24 or another ultrasound data path. For example, the beamformer 24 requests space in the memory 72 for storage of acquired ultrasound data, such as B-mode acoustic line data. In the example of B-mode operation, the request is for memory space for one or more lines or frames of B-mode data. In other examples, the request may be for space for one or more frames of B-mode information, one or more frames of color Doppler information and/or lines, frames or other appropriate groupings of other data. The amount of data, the division of the data, such as in packets corresponding to a line or other set of information, and the number of packets within any grouping or set of information is programmed by the CPU 74. As used herein, a group or set of information includes one or more packets of information.

In response to the request, the CPU 74 allocates one or more memory sections, such as 4 kilobyte sections of the memory 72, to store the ultrasound data (block 406 of FIG. 9). The allocated memory comprises one or more physically continuous or discontinuous 4 kilobyte or other size memory sections. Based on the physical address of the segments within the memory 72, the CPU 74 generates a Graphics Address Remapping Table (GART) or other address table for use in logical to physical address translation. The CPU 74 assigns logically contiguous ultrasound data packets in allocated memory 72 to various physical memory sections and stores the assignment in the GART. Preferably, the table comprises a list of physical addresses indexed by logical addresses, but other table structures may be used. Preferably, only upper physical address bits are stored in the table and correspond to 4 kbyte sections. The upper sequential (logical) address bits are used to index the table, which provides the upper physical address bits that are concatenated with lower sequential bits to form the full physical address. For 256 Mbytes of ultrasound image data, the translation table preferably contains 64K entries, and a 256 kilobyte table. Other size tables may be used.

The event ID is provided to the beamformer 24 to acknowledge and respond to the request for the allocation of memory. Preferably, the event ID is a 10-bit field, allowing, 1024 unique transfer events and allocated memory blocks to be concurrently used and managed by the CPU 74. Other size fields and numbers of transfer events may be used.

Based on the control information from the CPU 74 over the system bus 58, ultrasound data is acquired. For example, the ultrasound acoustic data acquisition path 60 obtains and processes ultrasound image information. When the processed ultrasound image information is ready for transfer to the memory 72, the ultrasound acoustic data acquisition path 60 generates a request for transfer to the data transfer controller 68. The request communicates a device identifier and the event ID to employ for generation of the logical address and control of the transfer operation.

In response to receiving the transfer request and event ID, the data transfer controller 68 transfers the ultrasound data over the ultrasound data bus 58. The data transfer controller 68 generates a starting address for each packet of data received from the ultrasound data bus 58 based on the transfer control parameters associated with the event ID. For B-mode and color Doppler mode ultrasound image data, the packet size is preferably associated with one acoustic line of data (e.g. 128–576 samples). For each successive packet associated with an event ID, the data transfer controller 68 computes the starting logical addresses. The packet associated with the last line of a frame or last packet for the event (multiple frames or less than one frame) preferably employs a unique event ID or passes a control bit to the data transfer controller 68 to signify the last transfer. This unique identification signifies completion of the transfer of ultrasound data associated with the event ID.

The interface device 70 receives the logically addressed ultrasound data from the data transfer controller 68 through the data port 80. The interface device 70 passes the ultrasound data to the memory 72 through the memory port 76. Preferably, the interface device 70 supports concurrent transfer of data between the CPU port 78 and the system port 82. Concurrent transfers from any two ports of the interface device 70 to other ports of the interface device 70 are also possible in alternative embodiments. The concurrent transfer of information through the interface device 70 reduces latency and improves data throughput.

In addition to concurrent routing as discussed above, the interface device 70 arbitrates and buffers data, such as ultrasound data or control data, destined for the same port of the interface device 70. For example, ultrasound data from the data port 80 is to be transferred to the memory port 76, and user interface or other data is to be transferred from the system port 82 to the memory port 76 at substantially the same time. The interface device 70 arbitrates by selecting data from either the data port 80 or system port 82 for transfer at a particular time. Concurrent transfers to the interface device 70 occur on both ports 80, 82, but then the interface device 70 arbitrates between the buffered data before writing to the memory 72. Information associated with the non-selected port, such as the system port 82, remains buffered. The buffered data is transferred when the memory port 76 is available. Preferably, the interface device 70 alternates between data from the data port 80 and the system port 82 for access to the memory port 76. On reads from the memory 72, arbitration occurs before the transfer, but alternatively, the interface device 70 reads ahead and locally buffers read data. The data is output from the buffer instead of accessing the memory port 76 to avoid arbitration. Arbitration between any two or more of the four ports of the interface device 70 for data transfers destined for any one of the ports for the interface device is possible.

In routing and transferring ultrasound data to the memory port 76 from the data port 80 of the interface device 70, the interface device 70 translates the logically addressed ultrasound image data addresses to physical memory addresses. Other addressing schemes and translation schemes may be used, such as providing translation with the data transfer controller 68. The translation scheme allows the allocation of large logically contiguous address ranges in physically discontinuous memory segments and permits the memory 72 to be efficiently utilized even where the process of allocation and deallocation of memory segments creates physically fragmented memory space. Preferably, the same logical to physical address translation is performed for any transfer of ultrasound data to or from the memory 72. The CPU 74, the data transfer controller 68 and the system bus 56 all access the same ultrasound data (data within the address range assigned to the data port 80) in the memory 72 using the same logical address scheme.

To translate the logical addresses to the physical addresses, the interface device 70 uses the GART or other table generated by the CPU 74. Preferably, the GART is stored in the memory 72 and contains address pointers for each 4 Kbyte physical memory segment. Preferably, the interface device 70 includes a memory for caching at least the last two or more translation table address pointers used (physical addresses). By caching a portion of the table, requiring access to the memory 72 for each address translation may be avoided. In alternative embodiments, the interface device 70 stores the entire table. As yet another alternative embodiment, physical address locations are assigned to the ultrasound data by the data transfer controller 68. Furthermore, a separate memory for storing the translation table may be used.

After a physical address is associated with each packet of ultrasound data, the interface device 70 transfers the ultrasound data to the memory 72 in a burst fashion. Other transfer techniques may be used. When performing transfers to or from the memory 72, the interface device 70 activates a bank of the memory and selects a particular page of one or more memory components. Successive transfers to or from the same page preferably occur on each successive clock cycle, when memory is comprised of SDRAM, to maximize the data transfer rate. For a memory port 76 employing a 64 bit wide data path and a 64 megahertz clock, transferring data on every clock yields a maximum data transfer bandwidth of 512 Mbytes/sec. Other data widths and clock speeds may be used. Interleaving burst transfers of ultrasound data to different pages in the same memory components requires additional overhead and reduces the effective bandwidth of the memory 72. By providing multiple blocks, each with multiple banks, in the memory 72 and transferring to a previously selected page, interleaving of burst transfers in different banks occurs with reduced overhead. Other interleaving techniques may be used.

Storing ultrasound image data in a large buffer, such as the memory 72, permits ultrasound image data acquisition, ultrasound image data processing by the CPU 74, and reconstruction processing to be decoupled, allowing disparate acquisition, processing and output data rates to be used.

Once the transfer of the ultrasound data to the data transfer controller 68 and the memory 72 is complete, the data transfer controller 68 generates an interrupt to the CPU indicating completion. In response to the interrupt, the CPU 74 performs ultrasound image data processing or otherwise makes the ultrasound image data in the memory 72 available for processing, such as reconstruction and display processing. The ultrasound image data is altered or further processed by the CPU 74 or provided directly to a video/audio acquisition data path 62 or the video/audio reconstruction data path 64. Alternatively, the ultrasound image data is transferred across the system bus 56 to one or more peripherals. Preferably, the CPU 74 performs additional processing on the ultrasound image data stored in the memory 72. This additional processing is done in real time or substantially concurrently with the acquisition or output of ultrasound image data. Alternatively, the CPU 74 processes the stored ultrasound image information not in real time.

The CPU 74 obtains the ultrasound image data from the memory 72 through the interface device 70. As discussed above, the CPU 74 generates logical addresses to acquire ultrasound image data stored from the data port 80. The interface device 70 translates the logical addresses to physical memory addresses. The ultrasound image data from the memory 72 is transferred to the CPU 74 for processing.

The CPU 74 spatially filters (e.g. 3 tap m-mode range video filtering or azimuthal filtering), temporally filters (e.g. single tap adaptive or recursive persistence), weights, applies a threshold to, or selects particular parameters of the ultrasound image data (block 410 of FIG. 9). The CPU 74 may also perform combinations of these and other processes 25, such as depth gain compensation, compression scaling, edge enhancement, noise and speckle filtering, peak map/ frame average processing, energy weighting of velocity, and non-real time compression and decompression of video data. The CPU 74 may generate or recover encoded information, such as format, color palettes, or other information for obtaining measurements from image data, for or from blanking gaps in VCR or video data. For depth gain compensation, background noise vectors are stored in the memory 72, and the CPU 74 inverts and smooths the vectors to determine the compensation. Other processes, such as performed by the ultrasound data acquisition path 60, the video/audio acquisition path 62 or the video/audio reconstruction path 64, may be performed by the CPU 74. Preferably, only lossless compression and decompression is performed, but lossy compression and decompression on static or real time images may be used. Additionally, any of the various processes performed by the CPU 74 may be performed in other ultrasound data paths.

Preferably, the CPU 74 uses a single instruction to operate on multiple pieces of data concurrently. This process is repeated for one or more instructions. With the preferred single instruction multiple data processor, 8 byte operands are processed in a single clock cycle at a 350 MHz clock rate. Some instructions operate at this level, but others operate on 4 word or 2 double word operands.

Depending on the amount of data processing and other bandwidth uses of the CPU 74, the data processing may be constrained under certain operating conditions, such as performing noise and speckle filtering on color Doppler data only when the flow sample count is greater than a required minimum. Changing the frame display rate may also limit or broaden the amount of data processing performed by the CPU 74. The attached Appendix A demonstrates code for temporally persisting B-mode data. The code is designed to test the amount of time a Pentium MMX processor uses to persist B-mode data. For implementation on the system 50, additional or different code may be used.

For static or non-real time compression by the CPU 74, NTSC 640×480 or PAL 786×576 full screen compression using DICOM (Packbits) or other lossless schemes may be used. For static compression, separate compressed data segments for each component are generated by the CPU 74. For RGB or YUV color spaces, three progressive files are generated.

For static or non-real time decompression by the CPU 74, RGB 4:4:4, YUV 4:4:4, or 4:0:0 (monochrome) data at a preferable pixel grid size of 768×576 or less is decompressed based on the compression schemes discussed above. The compressed data is either planar (separate scan segments for each component within the frame) or component interleaved (single scan segment with components interleaved). Preferably, the decompressed data is planar.

In addition to any processing of the ultrasound data, the CPU 74 generates text and graphics for display with the ultrasound image data (block 412 of FIG. 9). The text or graphics information is non-scrolling information, such as input selection information displayed to the user, patient information, calculated quantities and other text. The text and graphics information is stored in the memory 72 as text and graphics plane data. The CPU 74 also generates control plane data. The control plane data is stored in the memory 72.

In alternative embodiments, the CPU 74 performs other ultrasound data processing tasks. For example, the CPU 74 generates three-dimensional image constructions or representations. The CPU 74 obtains ultrasound image information in a video or acoustic format and manipulates the information to generate a three-dimensional representation. For example, the CPU 74 processes ultrasound image data from the beamformer 24 (e.g. I and Q values or detected data) to generate transducer positional information. This process is discussed in U.S. application Ser. No. 08/916,163 (pending), for an Ultrasonic Method for Imaging Blood Flow. As the three-dimensional representation or other data is generated by the CPU 74, the ultrasound data is stored in the memory 72. The ultrasound image data representing the three-dimensional construction or viewing planes associated with the three-dimensional reconstruction are stored in the memory 72 or output via the ultrasound data bus 58 for display.

For further discussion of the data processes performed by the CPU 74, see the attached Appendix D. In Appendix D, the CPU 74 is referred to as the Main Processor (MP) and the memory 72 is referred to as the main memory.

After storage in the memory 72, the ultrasound image data and other data is read out of the memory 72 for further processing, transfer through the peripheral interfaces 66, or transfer to other ultrasound data paths. Any of the ultrasound image or audio data stored in the memory 72, such as associated with different amounts of processing by ultrasound image data paths (including the CPU 74), is provided for display, further processing, or export. For example, the ultrasound image data provided by the video/audio acquisition path 62 or any other ultrasound image data path may be transferred from the memory 72 over the system bus 56 to any of various peripherals.

After one or more frames of ultrasound image data are ready for display, the CPU 74 communicates the availability to the video/audio reconstruction path 64 (block 408 of FIG. 9). The CPU 74 identifies the frame of data with the appropriate event ID, programs interface device 70 with the GART to obtain the ultrasound image data from the memory 72, and initializes the data transfer controller 68 for the type of transfer and starting logical address. The CPU 74 enables the video/audio reconstruction path 64, which generates a request for transfer of ultrasound image data. The request communicates the event ID to the data transfer controller 68. In response to the request, the data transfer controller 68 transfers the ultrasound image data from the memory 72 to the ultrasound data bus 58. Preferably, the image data is aligned on an acoustic or raster grid, but other grids may be used. Other information, such as text and graphics, control plane and waveform information is also transferred over the ultrasound data bus 58 to the video/audio reconstruction path 64. The video/audio reconstruction path 64 generates an image for the display 34 by combining the various display information, and generates audio by combining the various audio information.

As an alternative to acquiring ultrasound image data from the ultrasound acoustic data acquisition path 60 or outputting ultrasound image data to the video/audio reconstruction path 64, ultrasound image data is acquired or provided to the video/audio acquisition data path 62 or the peripheral interfaces 66. The transfers and processing of the ultrasound data discussed above are performed in the same or a similar manner.

Ultrasound data from two ore more different data paths, such as the ultrasound image acquisition path 60 and the video/audio acquisition data path 62 may occur substantially simultaneously. In this situation, the data transfer controller 68 arbitrates between requests for transfer and time interleaves ultrasound data packets on the data transfer bus 58 for transfer to or from the memory 72.

In a preferred embodiment, the transfers of ultrasound data over the ultrasound data bus 58 are managed by the CPU 74. Additionally, transfers of physio, or any other type of data stored in the memory 72 and transferred over the system bus 56 are managed by the CPU 74. The CPU 74 also manages the memory 72, including allocation and deallocation, assignment of event identifiers, GART loading, and data transfer controller 68 initialization and address generator table loading. The CPU 74 also dynamically directs the video/audio reconstruction data path 64 by identifying ultrasound data in the memory 72 for reconstruction. The packet sizes associated with any of the data, such as ultrasound data, audio data, patient information, text information, waveform information, control instructions may vary.

While the invention has been described above by reference to various embodiments, it would be understood that many changes and modifications can be made without departing from the scope of the invention. For example, an interface device 70 may have more or fewer ports. Other specifications and protocols may be used. More or less control and/or ultrasound image data processing may be performed by the CPU 74. Access to the memory may be provided without the interface device 70, such as through a memory port connected directly to various components.

It is therefore intended that the foregoing detailed description be understood as an illustration of the presently preferred embodiments of the invention, and not as a definition of the invention. It is only the following claims including all equivalents, that are intended to define the scope of this invention.

APPENDIX A

The following code implements recursive temporal persistence
for b-mode. The IIR coefficient alpha, a value from 0 to 1.0
is represented in hexadecimal by a 16-bit value from 0000 to 00FF.

The coefficient is copied 4 times and stored in the 64 bit
memory mapped coefficient registers, bper_alpha.

bper_alpha = alpha:alpha:alpha:alpha bper_1_minus_alpha = 0x0100010001000100-bper_alpha ptrx = pointer to stored x data ptry = pointer to previous frame y(frame_N-1)
and the pointer to the current outout y(frame_N)

note: y(frame_N-1) is destroyed iter    number of samples to process

The x and y data are stored in a packed byte format with
8 samples per 64 bit quad word.

The following MMX code fragment implements the persistence operation y(frame_N) = (1-alpha)* x + alpha * y(frame_N-1)

The code unpacks the 8 bit samples into 16 bit samples
performs the multiplies using the 16 bit multipliers on
the MMX capable Pentium class processors and then repacks, u,
the results into the 8 bit format.

Copyright Acuson Corporation  Nov 1997

```
        pxor    mm7,mm7             ;clear mm7
        movq mm6,bper_alpha
        movq mm5,bper_1_minus_alpha mov     esi,ptrx
        mov edi,ptry
        mov eax,iter
loop1:
                ; read x
                        movq mm1,[esi]
```

APPENDIX A

```
         movq mm0,mm1
         punpckhbw  mm1,mm7

; read y
         movq mm2,[edi]
         punpcklbw  mm0,mm7 movq mm3,mm2
         pmullw mm0,mm5 punpckhbw mm2,mm7
         pmullw mm1,mm5 punpcklbw mm3,mm7
         pmullw mm2,mm6 pmullw mm3,mm6 paddw  mm2,mm1 paddw  mm3,mm0
         psrlw  mm2,8 psrlw  mm3,8 packuswb  mm3,mm2
         add    esi,8

; write result
         movq [edi],mm3 add    edi,8
         sub    eax,1 jg  loop1
         emms           ; done
```

Appendix B
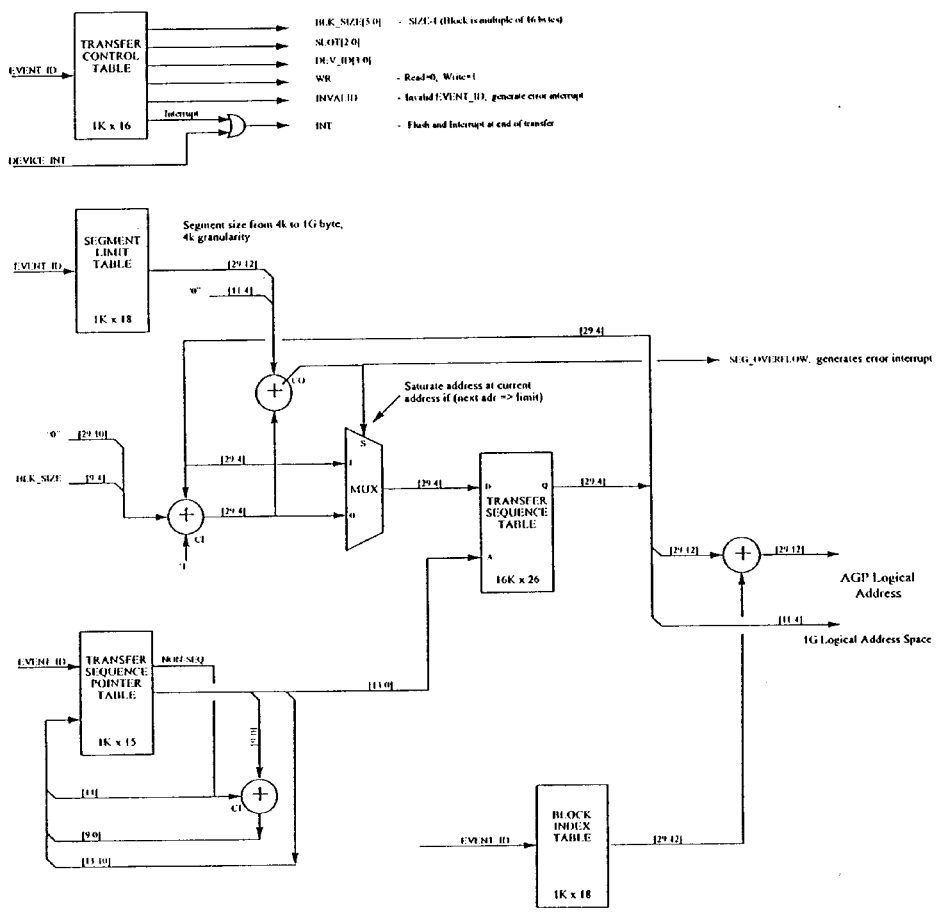

Appendix B
The following memory map identifies the location and size of each table within the DTC Address Generator RAM. CPU access to the RAM is interleaved with AGP address generation so that the CPU always has quick access to the RAM.
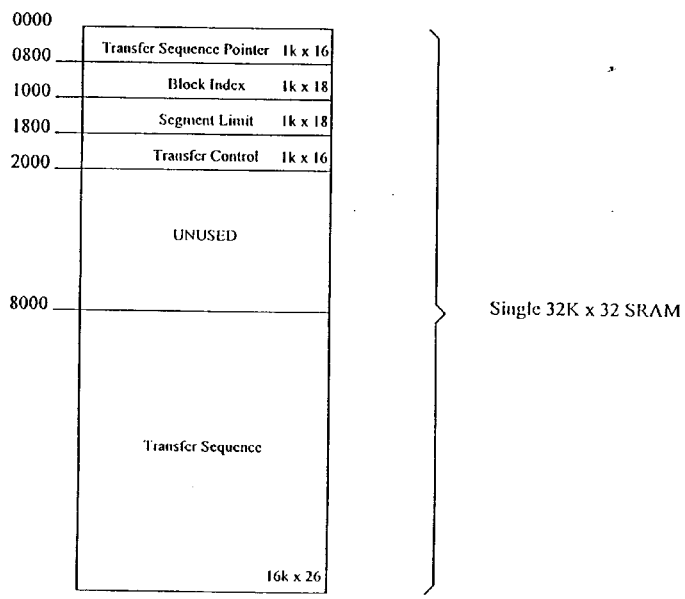

Appendix C

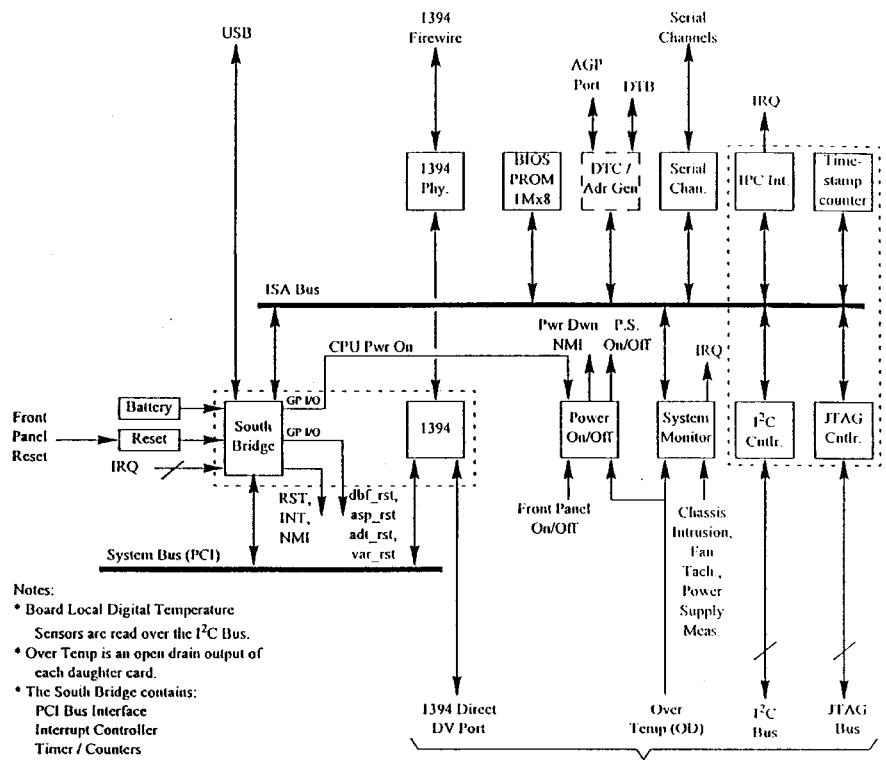

Notes:
* Board Local Digital Temperature Sensors are read over the I²C Bus.
* Over Temp is an open drain output of each daughter card.
* The South Bridge contains:
  PCI Bus Interface
  Interrupt Controller
  Timer / Counters
  USB Host Controller
  TOD Clock
  BB RAM (256 Bytes)
  PCI / ISA Bridge
  General Purpose I/O (CPU Pwr On, and board processor resets)
  System Reset The PCI / ISA bridge in the South Bridge component provides a 16 bit ISA standard local bus interface employed for access to the Data Transfer Controller (DTC) and Address Generator memory, and the following subsystem resources.
- BIOS EEPROM (1M x 8, aliased to high PCI address range)
- IPC Interrupt Controller
- Timestamp Counter
- Serial Channels (2 - dual UARTs)
- System Monitor
- I²C Serial Bus Controller
- JTAG Serial Bus Controller

Appendix C
The following ISA bus address map shows the address ranges for the BIOS PROM and other ISA Bus resident resources.
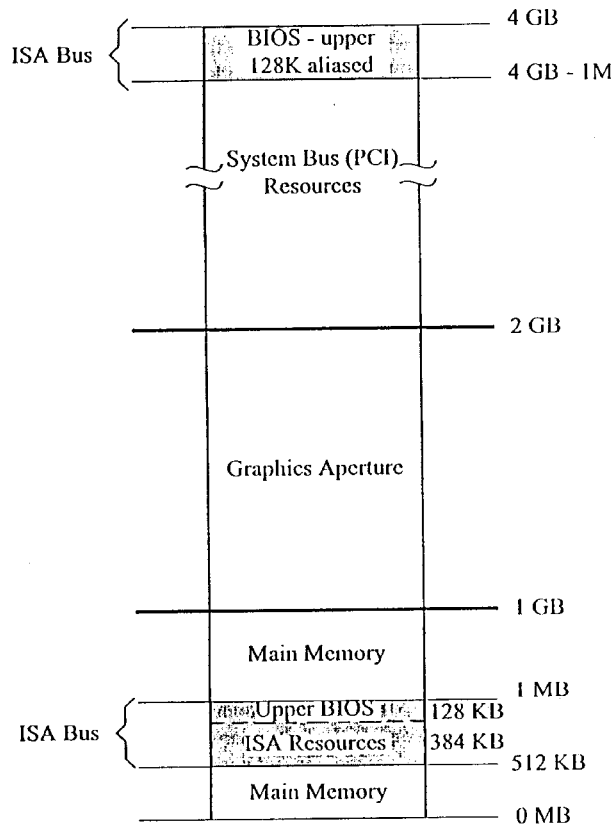

Appendix C

The BIOS EEPROM is a single 1M x 8 device containing AMB hardware identification and revision control information, boot code, power on diagnostics, device drivers, and all software not loaded from disk.

The IPC Interrupt Controller provides a 32 channel IPC interrupt facility for point to point communication directed at the Main CPU.

The Timestamp Counter is a 48 bit counter with time resolution of 20 usec. The ISA Bus is a 16 bit bus requiring the counter to be read in three consecutive word reads, the first of which will return the low word timestamp value and register the upper 32 bits in a register file addressed by ISA Bus address bits [5..3], which allows uniquely identifying up to eight devices with read access to the Timestamp Counter. Reads of the upper word fields will return values from the register file, allowing multiple devices unique address access to the high order successive values and permitting device interleaved read access of the Timestamp Counter without resource locking. Software arbitration will have to be employed if more than 8 devices or tasks require access.

The System Monitor block provides local temperature, chassis intrusion, fan tachometer, and power supply monitoring facilities. Values may be directly read for each monitored function, or programmable limit registers may be employed to interrupt the Main CPU for out of tolerance conditions. The System Monitor current implementation plan employs a National Semiconductor LM78 Microprocessor System Hardware Monitor IC, or similar device.

The JTAG and I$^2$C Bus serial bus controllers are resources residing on the ISA Bus through which the Main CPU performs board level serial scan diagnostics, ISP device programming, temperature sensing, and configuration data access.

APPENDIX D

B-MODE PERSISTENCE PROCESSING:

B-mode persistence will be implemented in software on the MP (Main Processor) using the MMX technology processing capability of the Pentium II processor. The routine will be hand-coded assembly language that can be called from C/C++. The routine takes packed 8-bit samples from two blocks of contiguously addressed memory and writes results to a third block. The routine implements the following IIR filtering equation on B-mode detected data (current frame data X and previous frame data Y):

$$Y(frame\_N) = (1-alpha) * X + alpha * Y(frame\_N-1)$$

The processor unpacks the 8 bit samples from Y and X into 16 bit samples, performs the multiplies using the 16 bit multipliers in the MMX pipeline, and then performs the adds and repacks the results into the 8 bit format before writing results back to main memory. All main memory accesses are quad words (64 bits/word).

The alpha and 1-alpha coefficients are stored and used with 8-bit precision and can range from 0 to 1.0.

The operations for an entire frame are started once the entire frame is available in the processor main memory. When complete, the entire processed frame will be available for scan conversion and display.

Processing rate:

The persistence operation must be performed in real time without excessive demand on the main processor (MP). Assuming that data comes out the ultrasound acoustic data acquisition path pipeline at a maximum of 10 Msamples per second (100 ns per sample) and if the CPU loading is limited to 20% maximum, then up to 20 ns per sample is provided to perform the persistence processing. The CPU can perform multiplies, adds, and other operations on 4 separate 16-bit values each in a single clock cycle.

Limit behavior:

Because intermediate frames data samples (Y) are stored with only 8-bit precision, a steady state DC input may not reach a correct value. It is most important that results reach a zero value to avoid low level "ghost" or "stuck" images. By truncating instead of rounding we always ensure an eventual return to zero from any value with zero input. Storing additional bits of intermediate results will remove this problem, but will cost significant CPU and memory cycles.

APPENDIX D

M-MODE VIDEO FILTERING:

The range video filtering is used in m-mode and is a combination of edge enhancement and low pass filtering. A selection of possible video filters (with a final grid of 1 lambda) are listed here:

vf1=[-0.0062 -0.3237 0.8299 0.8299 -0.3237 -0.0062];   % edge +1 7v3c vf2=[-0.0107 -0.4907 1.0000 1.0000 -0.4907 -0.0107];   % edge +1 5v2c vf3=[-0.0035 -0.2157 0.7192 0.7192 -0.2157 -0.0035];   % edge 0 5v2c vf4=[ -.0067 .0127 .02543 -.06361 -.04617 .30146 .55497
      .30146 -.04617 -.06361 .02543 .0127 -.0067 -.0006]; % edge -1 5v2c,3v2c vf5=[ -.00141 .00392 .01775 -.01373 -.07073 .02381 .30468 .47143
      .30468 .02381 -.07073 -.01373 .01775 .00392 -.00141];  % edge -1 7v3c Other user sharpness selections have pass-through video filters. The filters are selected by the user with the Sharpness key.

The edge enhancement filters (Filters vf1-3) are 6-taps each. These should be well within the capability of the MP. Assuming a 2 msec line firing period with 768 range samples, there are 2.6 microseconds per range sample. With 20% CPU loading, that gives 520 ns per point or about 86 ns per filter tap for the 6-tap case. The smoothing filters (filters 4 and 5) are longer, 14 and 15 taps, for about 35 ns per filter tap for the 15-tap case.

It is expected that the MP code which implements the m-mode video filtering will be C/C++ callable hand-coded MMX assembly. It will probably operate on small blocks (e.g. 50 msec) of m-mode data and will begin operations for a block after all data for a block has been acquired. Scan conversion will occur only after all video processing for the block is completed.

COLOR POST-DETECTION PROCESSING:

Color post processing will be implemented in software on the MP (Main Processor) using the MMX technology SIMD (single instruction, multiple data) processing pipeline of the CPU. The routines that performs this processing will be hand-coded assembly language routines that can be called from C/C++. The routines take in the detected color parameters from a block of main memory and output processed samples back into main memory for later scan conversion.

APPENDIX D

Detected data is stored into main memory into a 32 bit per sample format containing four packed detected parameters: Velocity (V), variance (S), energy (E) and unfiltered energy (U). In a 64 bit quadword, two color samples are read at a time arranged in the following format:

U2:E2:S2:V2:U1:E1:S1:V1

Intermediate results for use in temporal persistence are stored in a two quadword packed format, packing in 4 consecutive color range samples.

0:E4: 0:E3: 0:E2: 0:E1
S4:V4:S3:V3:S2:V2:S1:V1

The processsed results are written in a 4 sample per quadword format arranged and ready for scan conversion as follows:

V4:S4:V3:S3:V2:S2:V1:S1   for velocity-variance formats
or  V4:E4:V3:E3:V2:E2:V1:E1   for velocity-energy formats The operations for an entire frame are started once the entire frame is available in the processor main memory. When complete, the entire processed frame will be available for scan conversion and display.

Processing rate:

The operations for color post detection processing are completed in real time. The amount of time available for processing depends on the range grid, flow sample count and the number of b-mode and reverb lines (initializing transmitted acoustic lines for avoiding artifacts) for each flow group. The input data rate is less than or equal to the processing rate discounted by the maximum allocated CPU (MP) loading.

For example, with a range grid supporting quad beam with 100 ns per sample and a flow sample count of 6, a new detected flow data sample set is output from the beamformer and color detection stage as frequently as every 600 ns. For 20% CPU loading, the processor must process each detected sample within 120 ns.

Assuming 1 reverb line and 1 b-mode line for each flow group in the above case, then 160 ns per sample (20% loading and 800 ns per sample) is available to complete processing.

For conditions where the CPU does not have enough bandwidth, a mechanism for throttling back the beamformer is provided. This mechanism might be accomplished by reducing the data rate by inserting dead time between color

APPENDIX D

groups or frames or by changing the range or line grids. It is expected that this throttling back will occur only under extreme conditions. It is best that any throttling mechanism be open loop to avoid uneven frame acquisition rates (i.e. skipping).

PERSISTENCE:

Recursive temporal filtering is performed on the detected color parameters: log energy, velocity and variance. Unfiltered energy may or may not be persisted. The temporal filter is implemented as a single tap IIR filter with a parameter 'alpha' which determines the amount of filtering. The velocity and variance are processed with energy weighted persistence. The method of persistence is detailed in Acuson patent #5,609,155 Energy Weighted Parameter Spatial/Temporal Filter, the disclosure of which is herein incorporated by reference.

The IIR filter weight 'alpha' determines the values of log_alpha and log_alpha_m1.

log_alpha = -10*log10(alpha)

log_alpha_m1 = -10*log10(1.0 - alpha)

The alpha parameter depends on the user persistence setting as well as the calculated frame rate and typically ranges from 0 to about 0.86.

The energy weighted persistence values are computed as follows:

E1 = Enew - log_alpha

E2 = Eold - log_alpha_m1

Eout = 10 * log10 (10^(E1/10) + 10^(E2/10) )

beta = 10^(E1/10) / (10^(E1/10) + 10^(E2/10))

vel_out = beta * (Vnew - Vold) + Vold var_out = beta * (Vnew - Vold) + Vold

Eold = Eout

The energy values are all quantized to 0.5 dB steps. These functions are implemented in software using in-line mathematical functions:

APPENDIX D diff = E1 - E2

Eneout = max(E1,E2) - Fcorrection(|diff|)

where $$
\text{Fcorrection}(x) = \begin{array}{ll} 3 \text{ dB} & ; x == 0, 0.5 \\ 2.5 & ; x == 1, 1.5 \\ 2 & ; x == 2, 2.5, 3 \\ 1.5 & ; x == 3.5, 4, 4.5 \\ 1 & ; x == 5 .. 7 \\ 0.5 & ; x == 8 .. 12 \\ 0 & ; x >= 12.5 \end{array}
$$

The weighting factor for the velocity is computed using a two segment piecewise linear approximation:

beta = 0.3 * sat(0.13*diff) + 0.2 * sat(0.05*diff) + 0.5 where:

$$
\text{sat}(x) = \begin{array}{ll} x & ; -1<=x<=1 \\ 1 & ; x>1 \\ -1 & ; x<-1 \end{array}
$$

Other considerations:

The log energy is computed from the R(0) autocorrelation value. For the case where R(0) = 0, minus infinity is represented by another number -- a 38 bit unsigned number. This 114 dB dynamic range fits within 8-bit number with 0.5 dB resolution. However, the gap between R(0) equal to 0 and R(0) equal to 1 would be only about 14 dB. This is too small for proper behavior for all persistence cases. This can be addressed by specially detecting the energy value used for minus infinity and adjusting it downward by a large amount. The detection code for assigning the special value to something closer to minus infinity is expected only add a few additional processing cycles.

Non linear or adaptive persistence is implemented, if used, with a small number of additional processing cycles. The log_alpha and log_alpha_m1 values would depend on a magnitude comparison of Eold. A patent for this function was applied for Dec 1994 by Arenson et al (See U.S. Application Serial No. 08/827,863).

APPENDIX D

THRESHOLDING:

The threshold operations typically consist of various combinations of lower energy, velocity, variance and upper energy and unfiltered energy thresholds and depend on the color mode: CDV (velocity), CDE (energy), DTV (tissue velocity), or DTA (tissue acceleration).

There will probably be one major routine for each color mode with the threshold algorithm hard coded in to maximize performance. The threshold levels are usually filter and transducer dependent. Typically, one algorithm can work for all modes, although multiple algorithms will be supported. Cache use and total execution time are considerations for how the algorithms will finally be implemented.

The lower energy threshold is relative to the noise floor--the background noise vector. The processing necessary to create a smooth and usable noise vector is performed. This entails spatial and temporal filtering of the detected noise energy values.

SCALING:

The scaling operations are used in the energy modes. The log detected energy and the depth variable offset (gain) are added. The dynamic range of the signal is compressed down to the desired user-controlled dynamic range (i.e between 10 and 80 dB).

The background noise dependent energy depth gain compensation used in CDE mode will also be supported.

AZIMUTHAL SPATIAL SMOOTHING:

The next operation in the processing chain is azimuthal spatial smoothing. A beam variable kernel allows user variable smoothing (sharpness) as well as automatic compensation for geometric distortion from multibeam. A patent disclosing beam variable filtering was applied for by Greg Holley and Ismayil Guracar in April 1996 (See U.S. Application Serial No. 08/638,384).

The spatial smoothing operation is performed on the two parameters selected for display. It is possible to have different smoothing coefficients for the different parameters.

The filter will be a 3 or 4 tap kernel with positive coefficients. This will be implemented as 3 pairs of bilinear filter operations. The velocity smoothing must account for minimum arc when interpolating each pair of velocities.

The smoothing kernel collapses at the boundaries. The same number of lines go into the filter as come out.

APPENDIX D

RANGE SPATIAL SMOOTHING:

5   The range spatial smoothing is an operator selected and range grid dependent function. It is likely to be coarsely controlled with few taps and a small range of coefficient values.

OTHER PROCESSING FUNCTIONS:

10  A noise and speckle filter is a 3x3 sample grid filter which removes lone noise samples as well as fills in missing samples or holes. This improves image presentation and results in a few dB of additional apparent SNR. Without this filter, there would have to be a few additional dBs of SNR to get similar image appearance and quality. Some of the longer flow sample counts may allow this feature to be used in some cases.
15
COLOR M-MODE:

Color m-mode post detection processing is quite similar to the 2D processing. Temporal persistence or azimuthal spatial smoothing operations may or may not be
20  performed. Since the maximum line period for color m-mode is probably greater than 1 msec, several microseconds are likely available to process each range sample with little CPU loading. Separate processing routines for color m-mode as well as for each scanning mode (i.e. CDV, CDE, DTV, etc) may be used.

What is claimed is:

1. An ultrasound apparatus for processing ultrasound data, the apparatus comprising:
an interface device comprising a memory port, a processor port, an ultrasound data port and a system port;
a memory operatively connected to the memory port;
a processor operatively connected to the processor port;
a source of acoustic data operatively connected to the ultrasound data port; and
a system bus operatively connected to the system port;
wherein the memory substantially concurrently stores data from the processor, ultrasound data from the source, and data from the system bus; and wherein the processor has direct access to the memory.

2. The apparatus of claim 1 wherein the system bus has direct access to the memory.

3. The apparatus of claim 1 wherein:
the memory stores instruction data for the processor; and
the data from the processor comprises processed ultrasound data.

4. The apparatus of claim 1 wherein the memory is operable to provide data to the source, the processor and the system bus.

5. The apparatus of claim 1 wherein the memory comprises a Synchronous DRAM device.

6. The apparatus of claim 1 wherein the memory comprises a RAMBUS device.

7. The apparatus of claim 1 wherein the memory comprises at least two memory banks, the at least two memory banks operatively connected to the memory port.

8. The apparatus of claim 1 wherein the processor comprises a single instruction, multiple data capable processor.

9. The apparatus of claim 8 wherein the processor comprises a multimedia extension processor.

10. The apparatus of claim 8 wherein the processor further comprises a cache memory and a host bus, the host bus operatively connected to the processor port.

11. The apparatus of claim 1 wherein the source comprises a transfer controller.

12. The apparatus of claim 11 wherein the transfer controller comprises a device operable pursuant to an Accelerated Graphics Port Interface Specification.

13. The apparatus of claim 11 wherein the transfer controller comprises a buffer.

14. The apparatus of claim 1 wherein the source comprises a data bus.

15. The apparatus of claim 14 wherein the data bus is operable to transfer ultrasound image data selected from the group consisting of: B-mode data, M-mode data, beamformer data, color Doppler data, Spectral Doppler data, and combinations thereof.

16. The apparatus of claim 14 wherein the data bus comprises a path operable to transfer ultrasound data selected from the group consisting of: acoustic image data and video data.

17. The apparatus of claim 1 wherein at least one peripheral interface operatively connects to the system bus, and at least one peripheral operatively connects to the at least one peripheral interface.

18. The apparatus of claim 1 wherein the memory stores text plane data.

19. The apparatus of claim 1 wherein the memory stores a table of physical memory addresses.

20. The apparatus of claim 17 wherein the at least one peripheral interface comprises an interface selected from the group consisting of: a RS-232 serial interface, an IEEE Std. 1394-1995 interface, a Universal Serial Bus interface, an Ethernet 10/100 Base T interface, and an industry standard interface.

21. The apparatus of claim 17 wherein the at least one peripheral comprises a peripheral selected from the group of: a video cassette recorder, a printer, a camera, a physio module, a hard disk drive, a removable media storage device, a user interface, a Local Area Network connection, and combinations thereof.

22. The apparatus of claim 1 wherein the interface device comprises a device operable pursuant to an Accelerated Graphic Port specification.

23. The apparatus of claim 1 wherein the interface device comprises a Quad Port Acceleration device.

24. The apparatus of claim 1 wherein:
at least one peripheral interface operatively connects to the system bus, and at least one peripheral operatively connects to the at least one peripheral interface;
the source comprises a data transfer controller and a data bus for transferring ultrasound image data selected from the group consisting of: acquired acoustic data, acquired video data, display acoustic data for reconstruction and combinations thereof;
wherein the memory stores instruction data for the processor; and
further comprising a display device operatively connected to the data bus.

25. A method for processing ultrasound data in an ultrasound system, the method comprising the steps of:
(a) connecting an interface device comprising a memory port, a processor port, an ultrasound data port and a system port to a memory, a processor, a source of ultrasound image data and a system bus, the memory operatively connected to the memory port, the processor operatively connected to the processor port, the source of ultrasound data operatively connected to the ultrasound data port, and the system bus operatively connected to the system port;
(b) storing data from a processor, ultrasound image data from the source, and data from a system bus in a memory; and
(c) providing direct access by the processor to the memory.

26. The method of claim 25 further comprising the step (d) of providing direct access by the system bus to the memory.

27. The method of claim 25 wherein the step (c) comprises transferring data between the processor and the memory in response to one bus transaction.

28. The method of claim 25:
further comprising the step (d) of storing instruction code data for the processor in the memory; and
wherein the step (b) comprises storing processed ultrasound image data from the processor.

29. The apparatus of claim 25 further comprising the step (d) of providing data to the source, the processor and the system bus from the memory.

30. The method of claim 25 wherein the step (a) comprises connecting a single instruction, multiple data capable processor.

31. The method of claim 25 further comprising the step (d) of operating the data port pursuant to an Accelerated Graphics Port Interface Specification.

32. The method of claim 25 further comprising the step (d) of transferring ultrasound image data selected from the group consisting of: B-mode data, M-mode data, beamformer data, color Doppler data, Spectral Doppler data, and combinations thereof with the source, the source comprising a data bus.

33. The method of claim 32 wherein the step (d) comprises transferring data selected from the group consisting of: acoustic image data and video data.

34. The method of claim 26 further comprising the steps of:
   (d) operatively connecting at least one peripheral interface to the system bus and at least one peripheral to the at least one peripheral interface; and
   (e) transferring data between the at least one peripheral and the memory.

35. The method of claim 34 wherein the step (e) comprises transferring physio module data to the memory.

36. The method of claim 25 further comprising the step (d) of operating the data port pursuant to an Accelerated Graphic Port specification.

37. The method of claim 25 further comprising the step (d) of storing text plane data in the memory.

38. The method of claim 25 wherein the step (c) comprises storing a table of physical memory addresses in the memory.

39. An ultrasound apparatus for processing ultrasound data, the apparatus comprising:
   an interface device comprising a memory port, a processor port, on ultrasound data port and a system port;
   a memory operatively connected to the memory port;
   a processor operatively connected to the processor port;
   a source of ultrasonic data operatively connected to the ultrasound data port; and
   a system bus operatively connected to the system port;
   wherein the memory substantially concurrently stores data from the processor, ultrasound data from the source, and data from the system bus; and wherein the system bus has direct access to the memory.

40. The apparatus of claim 39 wherein the processor has direct access to the memory.

41. A method for processing ultrasound data in an ultrasound system, the method comprising the steps of:
   (a) connecting an interface device comprising a memory port, a processor port, an ultrasound data port and a system port to a memory, a processor, a source of ultrasonic data and a system bus, the memory operatively connected to the memory port, the processor operatively connected to the processor port, the source of ultrasound data operatively connected to the ultrasound data port, and the system bus operatively connected to the system port;
   (b) storing data from a processor, ultrasound data from a source, and data from a system bus in a memory; and
   (c) providing direct access by the system bus to the memory.

* * * * *